(12) United States Patent
Altshuler et al.

(10) Patent No.: US 8,915,948 B2
(45) Date of Patent: Dec. 23, 2014

(54) METHOD AND APPARATUS FOR PHOTOTHERMAL TREATMENT OF TISSUE AT DEPTH

(75) Inventors: Gregory B. Altshuler, Lincoln, MA (US); Andrei V. Erofeev, North Andover, MA (US); Henry Zenzie, Dover, MA (US); Richard Rox Anderson, Boston, MA (US); Dieter Manstein, Boston, MA (US); James Burke, III, Londonderry, NH (US); Andrew Radl, Barrington, NH (US); Michael Z. Smirnov, Burlington, MA (US)

(73) Assignees: Palomar Medical Technologies, LLC, Westford, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/032,004

(22) Filed: Feb. 15, 2008

(65) Prior Publication Data

US 2009/0024193 A1 Jan. 22, 2009

Related U.S. Application Data

(63) Continuation of application No. 10/465,137, filed on Jun. 19, 2003, now Pat. No. 7,351,252.

(60) Provisional application No. 60/389,871, filed on Jun. 19, 2002.

(51) Int. Cl.
*A61N 5/06* (2006.01)
*A61B 5/00* (2006.01)
(Continued)

(52) U.S. Cl.
CPC ............... *A61B 5/6843* (2013.01); *A61N 7/00* (2013.01); *A61B 2018/00452* (2013.01); *A61B 2018/00476* (2013.01); *A61N 1/32* (2013.01); *A61B 2018/00458* (2013.01); *A61N 2007/0008* (2013.01); *A61B 2018/00011* (2013.01); *A61B 2018/00005* (2013.01); *A61N 5/0613* (2013.01); *A61B 18/203* (2013.01); *A61B 18/14* (2013.01)
USPC .................. 607/88; 607/89; 128/898

(58) Field of Classification Search
USPC ............ 606/3–29, 88–94, 96–103, 115; 607/88–92; 601/84, 85, 89, 97, 601/100–104; 128/898
See application file for complete search history.

(56) References Cited

U.S. PATENT DOCUMENTS

| 853,033 A | 5/1907 | Roberts |
| 1,590,283 A | 6/1926 | Catlin |

(Continued)

FOREIGN PATENT DOCUMENTS

| AT | 400305 | 4/1995 |
| AU | 1851583 | 3/1984 |

(Continued)

OTHER PUBLICATIONS

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008).

(Continued)

*Primary Examiner* — Ahmed Farah
(74) *Attorney, Agent, or Firm* — Thomas J. Engellenner; Reza Mollaaghababa; Pepper Hamilton LLP

(57) ABSTRACT

The present invention provides method and apparatus for treating tissue in a region at depth by applying optical radiation thereto of a wavelength able to reach the depth of the region and of a selected relatively low power for a duration sufficient for the radiation to effect the desired treatment while concurrently cooling tissue above the selected region to protect such tissue. Treatment may be enhanced by applying mechanical, acoustic or electrical stimulation to the region.

56 Claims, 5 Drawing Sheets

(51) Int. Cl.
*A61B 18/20* (2006.01)
*A61N 7/00* (2006.01)
*A61B 18/00* (2006.01)
*A61N 1/32* (2006.01)
*A61B 18/14* (2006.01)

(56) References Cited

U.S. PATENT DOCUMENTS

| | | |
|---|---|---|
| 1,676,183 A | 7/1928 | Garfunkle |
| 1,706,161 A | 3/1929 | Hollnagel |
| 2,068,721 A | 1/1937 | Wappler et al. |
| 2,472,385 A | 6/1949 | Rollman |
| 2,669,771 A | 2/1954 | Burge et al. |
| 3,243,650 A | 3/1966 | Hawkins et al. |
| 3,261,978 A | 7/1966 | Brenman |
| 3,284,665 A | 11/1966 | Goncz |
| 3,327,712 A | 6/1967 | Kaufman et al. |
| 3,465,203 A | 9/1969 | Michaels et al. |
| 3,486,070 A | 12/1969 | Engel |
| 3,524,144 A | 8/1970 | Buser et al. |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,651,425 A | 3/1972 | McKnight |
| 3,653,778 A | 4/1972 | Freiling |
| 3,667,454 A | 6/1972 | Prince |
| 3,693,623 A | 9/1972 | Harte et al. |
| 3,699,967 A | 10/1972 | Anderson |
| 3,725,733 A | 4/1973 | Mack et al. |
| 3,766,393 A | 10/1973 | Herzog et al. |
| 3,766,488 A | 10/1973 | Kohn |
| 3,769,963 A | 11/1973 | Goldman et al. |
| 3,793,723 A | 2/1974 | Kuris et al. |
| 3,794,028 A | 2/1974 | Mueller et al. |
| 3,815,046 A | 6/1974 | Johnson et al. |
| 3,818,373 A | 6/1974 | Chun et al. |
| 3,818,914 A | 6/1974 | Bender |
| 3,821,510 A | 6/1974 | Muncheryan |
| 3,834,391 A | 9/1974 | Block |
| 3,843,865 A | 10/1974 | Nath |
| 3,846,811 A | 11/1974 | Nakamura et al. |
| 3,857,015 A | 12/1974 | Clark et al. |
| 3,858,577 A | 1/1975 | Bass et al. |
| 3,885,569 A | 5/1975 | Judson |
| 3,890,537 A | 6/1975 | Park et al. |
| 3,900,034 A | 8/1975 | Katz |
| 3,909,649 A | 9/1975 | Arsena |
| 3,914,709 A | 10/1975 | Pike et al. |
| 3,939,560 A | 2/1976 | Lyall |
| 3,977,083 A | 8/1976 | Leslie et al. |
| 3,980,861 A | 9/1976 | Fukunaga |
| 4,019,156 A | 4/1977 | Fountain et al. |
| 4,037,136 A | 7/1977 | Hoene |
| 4,038,984 A | 8/1977 | Sittner |
| 4,047,106 A | 9/1977 | Robinson |
| 4,065,370 A | 12/1977 | Noble et al. |
| 4,122,853 A | 10/1978 | Smith |
| 4,133,503 A | 1/1979 | Bliss |
| 4,139,342 A | 2/1979 | Sheldrake et al. |
| 4,154,240 A | 5/1979 | Ikuno et al. |
| 4,176,324 A | 11/1979 | Aldag et al. |
| 4,188,927 A | 2/1980 | Harris |
| 4,213,462 A | 7/1980 | Sato |
| 4,228,800 A | 10/1980 | Degler, Jr. et al. |
| 4,233,493 A | 11/1980 | Nath |
| 4,254,333 A | 3/1981 | Bergstrom |
| 4,269,067 A | 5/1981 | Tynan et al. |
| 4,273,109 A | 6/1981 | Enderby |
| 4,275,335 A | 6/1981 | Ishida |
| 4,291,281 A | 9/1981 | Pinard et al. |
| 4,292,601 A | 9/1981 | Aldag et al. |
| 4,293,827 A | 10/1981 | McAllister et al. |
| 4,298,005 A | 11/1981 | Mutzhas |
| 4,302,730 A | 11/1981 | Jernigan |
| 4,313,431 A | 2/1982 | Frank |
| 4,316,467 A | 2/1982 | Muckerheide |
| 4,333,197 A | 6/1982 | Kuris |
| 4,335,726 A | 6/1982 | Kolstedt |
| 4,336,809 A | 6/1982 | Clark |
| 4,364,015 A | 12/1982 | Drake et al. |
| 4,375,684 A | 3/1983 | Everett |
| 4,388,924 A | 6/1983 | Weissman et al. |
| 4,409,479 A | 10/1983 | Sprague et al. |
| 4,435,808 A | 3/1984 | Javan |
| 4,445,217 A | 4/1984 | Acharekar et al. |
| 4,452,081 A | 6/1984 | Seppi |
| 4,456,872 A | 6/1984 | Froeschle |
| 4,461,294 A | 7/1984 | Baron |
| 4,488,104 A | 12/1984 | Suzuki |
| 4,489,415 A | 12/1984 | Jones et al. |
| 4,503,854 A | 3/1985 | Jako |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A * | 9/1985 | Nath et al. .................. 606/3 |
| 4,553,546 A | 11/1985 | Javelle |
| 4,555,786 A | 11/1985 | Byer |
| 4,559,943 A | 12/1985 | Bowers |
| 4,561,440 A | 12/1985 | Kubo et al. |
| 4,566,271 A | 1/1986 | French et al. |
| 4,566,438 A | 1/1986 | Liese et al. |
| 4,569,345 A | 2/1986 | Manes |
| 4,576,177 A | 3/1986 | Webster, Jr. |
| 4,587,968 A | 5/1986 | Price |
| 4,591,762 A | 5/1986 | Nakamura |
| 4,592,353 A | 6/1986 | Daikuzono |
| 4,601,037 A | 7/1986 | McDonald |
| 4,601,753 A | 7/1986 | Soileau et al. |
| 4,608,978 A | 9/1986 | Rohr |
| 4,608,979 A | 9/1986 | Breidenthal et al. |
| 4,617,926 A | 10/1986 | Sutton |
| 4,623,929 A | 11/1986 | Johnson et al. |
| 4,629,884 A | 12/1986 | Bergstrom |
| 4,638,800 A | 1/1987 | Michel |
| 4,653,495 A | 3/1987 | Nanaumi |
| 4,656,641 A | 4/1987 | Scifres et al. |
| 4,662,368 A | 5/1987 | Hussein et al. |
| 4,677,347 A | 6/1987 | Nakamura et al. |
| 4,686,986 A | 8/1987 | Fenyo et al. |
| 4,693,244 A | 9/1987 | Daikuzono |
| 4,693,556 A | 9/1987 | McCaughan, Jr. |
| 4,695,697 A | 9/1987 | Kosa |
| 4,710,677 A | 12/1987 | Halberstadt et al. |
| 4,718,416 A | 1/1988 | Nanaumi |
| 4,724,835 A | 2/1988 | Liss et al. |
| 4,733,660 A | 3/1988 | Itzkan |
| 4,735,201 A | 4/1988 | O'Reilly |
| 4,736,743 A | 4/1988 | Daikuzono |
| 4,736,745 A | 4/1988 | Gluckman |
| 4,740,047 A | 4/1988 | Abe et al. |
| 4,745,909 A | 5/1988 | Pelton et al. |
| 4,747,660 A | 5/1988 | Nishioka et al. |
| 4,749,913 A | 6/1988 | Stuermer et al. |
| 4,759,349 A | 7/1988 | Betz et al. |
| 4,773,413 A | 9/1988 | Hussein et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,813,412 A | 3/1989 | Yamazaki et al. |
| 4,813,762 A | 3/1989 | Leger et al. |
| 4,819,669 A | 4/1989 | Politzer |
| 4,826,431 A | 5/1989 | Fujimura et al. |
| 4,829,262 A | 5/1989 | Furumoto |
| 4,832,024 A | 5/1989 | Boussignac et al. |
| 4,840,174 A | 6/1989 | Gluckman |
| 4,840,563 A | 6/1989 | Altendorf |
| 4,845,608 A | 7/1989 | Gdula |
| 4,848,339 A | 7/1989 | Rink et al. |
| 4,852,107 A | 7/1989 | Hamal et al. |
| 4,852,549 A | 8/1989 | Mori et al. |
| 4,860,172 A | 8/1989 | Schlager et al. |
| 4,860,303 A | 8/1989 | Russell |

(56) References Cited

U.S. PATENT DOCUMENTS

| | | |
|---|---|---|
| 4,860,743 A | 8/1989 | Abela |
| 4,860,744 A | 8/1989 | Johnson et al. |
| 4,862,886 A | 9/1989 | Clarke et al. |
| 4,862,888 A | 9/1989 | Yessik |
| 4,862,903 A | 9/1989 | Campbell |
| 4,871,479 A | 10/1989 | Bachelard et al. |
| 4,878,224 A | 10/1989 | Kuder |
| 4,884,560 A | 12/1989 | Kuracina |
| 4,887,600 A | 12/1989 | Watson et al. |
| 4,889,525 A | 12/1989 | Yuhas et al. |
| 4,890,898 A | 1/1990 | Bentley et al. |
| 4,891,817 A | 1/1990 | Duarte |
| 4,896,329 A | 1/1990 | Knaak |
| 4,898,438 A | 2/1990 | Mori |
| 4,898,439 A | 2/1990 | Mori |
| 4,901,323 A | 2/1990 | Hawkins et al. |
| 4,905,690 A | 3/1990 | Ohshiro et al. |
| 4,910,438 A | 3/1990 | Farnsworth |
| 4,913,142 A | 4/1990 | Kittrell et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,931,053 A | 6/1990 | L'Esperance |
| 4,932,954 A | 6/1990 | Wondrazek et al. |
| 4,945,239 A | 7/1990 | Wist et al. |
| 4,950,266 A | 8/1990 | Sinofsky |
| 4,955,882 A | 9/1990 | Hakky |
| 4,968,314 A | 11/1990 | Michaels |
| 4,972,427 A | 11/1990 | Streifer et al. |
| 4,973,848 A | 11/1990 | Kolobanov et al. |
| 4,976,308 A | 12/1990 | Faghri |
| 4,976,709 A | 12/1990 | Sand |
| 4,977,571 A | 12/1990 | Furumoto et al. |
| 4,978,186 A | 12/1990 | Mori |
| 4,979,180 A | 12/1990 | Muncheryan |
| 4,992,256 A | 2/1991 | Skaggs et al. |
| 4,994,060 A | 2/1991 | Rink et al. |
| 5,000,752 A | 3/1991 | Hoskin et al. |
| 5,006,293 A | 4/1991 | Hartman et al. |
| 5,009,658 A | 4/1991 | Damgaard-Iversen |
| 5,011,483 A | 4/1991 | Sleister |
| 5,027,359 A | 6/1991 | Leger et al. |
| 5,030,090 A | 7/1991 | Maeda et al. |
| 5,032,178 A | 7/1991 | Cornell |
| 5,037,421 A | 8/1991 | Boutacoff et al. |
| 5,041,109 A | 8/1991 | Abela |
| 5,046,494 A | 9/1991 | Searfoss et al. |
| 5,050,597 A | 9/1991 | Daikuzono |
| 5,056,515 A | 10/1991 | Abel |
| 5,057,099 A | 10/1991 | Rink |
| 5,057,104 A | 10/1991 | Chess |
| 5,059,192 A | 10/1991 | Zaias |
| 5,061,266 A | 10/1991 | Hakky |
| 5,065,515 A | 11/1991 | Iderosa |
| 5,066,292 A | 11/1991 | Müller et al. |
| 5,066,293 A | 11/1991 | Furumoto |
| 5,071,416 A | 12/1991 | Heller et al. |
| 5,071,417 A | 12/1991 | Sinofsky |
| 5,080,660 A | 1/1992 | Buelna |
| 5,090,019 A | 2/1992 | Scheps |
| 5,092,865 A | 3/1992 | Rink |
| 5,102,410 A | 4/1992 | Dressel |
| 5,108,388 A | 4/1992 | Trokel |
| 5,109,387 A | 4/1992 | Garden et al. |
| 5,112,328 A | 5/1992 | Taboada et al. |
| 5,127,395 A | 7/1992 | Bontemps |
| 5,129,896 A | 7/1992 | Hasson |
| 5,129,897 A | 7/1992 | Daikuzono |
| 5,132,980 A | 7/1992 | Connors et al. |
| 5,133,102 A | 7/1992 | Sakuma et al. |
| 5,137,530 A | 8/1992 | Sand |
| 5,140,608 A | 8/1992 | Karpol et al. |
| 5,140,984 A | 8/1992 | Dew et al. |
| 5,147,353 A | 9/1992 | Everett |
| 5,147,356 A | 9/1992 | Bhatta |
| 5,151,097 A | 9/1992 | Daikuzono |
| 5,159,601 A | 10/1992 | Huber |
| 5,160,194 A | 11/1992 | Feldman |
| 5,163,935 A | 11/1992 | Black et al. |
| 5,171,564 A | 12/1992 | Nathoo et al. |
| 5,178,617 A | 1/1993 | Kuizenga et al. |
| 5,180,378 A | 1/1993 | Kung et al. |
| 5,182,557 A | 1/1993 | Lang |
| 5,182,857 A | 2/1993 | Simon |
| 5,190,541 A | 3/1993 | Abele et al. |
| 5,191,883 A | 3/1993 | Lennox et al. |
| 5,192,278 A | 3/1993 | Hayes et al. |
| 5,193,526 A | 3/1993 | Daikuzono |
| 5,196,004 A | 3/1993 | Sinofsky |
| 5,197,470 A | 3/1993 | Helfer et al. |
| 5,201,731 A | 4/1993 | Hakky |
| 5,207,671 A | 5/1993 | Franken et al. |
| 5,207,672 A | 5/1993 | Roth et al. |
| 5,207,673 A | 5/1993 | Ebling et al. |
| 5,209,748 A | 5/1993 | Daikuzono |
| 5,213,092 A | 5/1993 | Uram |
| 5,217,455 A | 6/1993 | Tan |
| 5,219,347 A | 6/1993 | Negus et al. |
| 5,222,907 A | 6/1993 | Katabuchi et al. |
| 5,222,953 A | 6/1993 | Dowlatshaki |
| 5,225,926 A | 7/1993 | Cuomo et al. |
| 5,226,907 A | 7/1993 | Tankovich |
| 5,242,437 A | 9/1993 | Everett et al. |
| 5,242,438 A | 9/1993 | Saadatmanesh |
| 5,246,436 A | 9/1993 | Rowe |
| 5,249,192 A | 9/1993 | Kuizenga et al. |
| 5,254,114 A | 10/1993 | Reed, Jr. et al. |
| 5,255,277 A | 10/1993 | Carvalho |
| 5,257,970 A | 11/1993 | Dougherty |
| 5,257,991 A | 11/1993 | Fletcher et al. |
| 5,261,904 A | 11/1993 | Baker et al. |
| 5,267,399 A | 12/1993 | Johnston |
| 5,267,995 A | 12/1993 | Doiron et al. |
| 5,267,998 A | 12/1993 | Hagen |
| 5,269,777 A | 12/1993 | Doiron et al. |
| 5,269,780 A | 12/1993 | Roos |
| 5,281,211 A | 1/1994 | Parel et al. |
| 5,281,216 A | 1/1994 | Klicek |
| 5,282,797 A | 2/1994 | Chess |
| 5,284,154 A | 2/1994 | Raymond et al. |
| 5,287,372 A | 2/1994 | Ortiz |
| 5,287,380 A | 2/1994 | Hsia |
| 5,290,273 A | 3/1994 | Tan |
| 5,290,274 A | 3/1994 | Levy et al. |
| 5,292,320 A | 3/1994 | Brown et al. |
| 5,293,880 A | 3/1994 | Levitt |
| 5,300,063 A | 4/1994 | Tano et al. |
| 5,300,065 A | 4/1994 | Anderson |
| 5,300,097 A | 4/1994 | Lerner et al. |
| 5,303,585 A | 4/1994 | Lichte |
| 5,304,167 A | 4/1994 | Freiberg |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,307,369 A | 4/1994 | Kimberlin |
| 5,308,311 A | 5/1994 | Eggers et al. |
| 5,312,395 A | 5/1994 | Tan et al. |
| 5,312,396 A | 5/1994 | Feld et al. |
| 5,320,618 A | 6/1994 | Gustafsson |
| 5,320,620 A | 6/1994 | Long et al. |
| 5,330,470 A | 7/1994 | Hagen |
| 5,331,649 A | 7/1994 | Dacquay et al. |
| 5,334,191 A | 8/1994 | Poppas et al. |
| 5,334,193 A | 8/1994 | Nardella |
| 5,336,217 A | 8/1994 | Buys et al. |
| 5,336,221 A | 8/1994 | Anderson |
| 5,342,358 A | 8/1994 | Daikuzono et al. |
| 5,344,418 A | 9/1994 | Ghaffari |
| 5,344,434 A | 9/1994 | Talmore |
| 5,346,488 A | 9/1994 | Prince et al. |
| 5,348,551 A | 9/1994 | Spears et al. |

(56) References Cited

U.S. PATENT DOCUMENTS

| | | |
|---|---|---|
| 5,349,590 A | 9/1994 | Amirkhanian et al. |
| 5,350,376 A | 9/1994 | Brown |
| 5,353,020 A | 10/1994 | Schurmann |
| 5,353,790 A | 10/1994 | Jacques et al. |
| 5,354,294 A | 10/1994 | Chou |
| 5,356,081 A | 10/1994 | Sellar |
| 5,358,503 A | 10/1994 | Bertwell et al. |
| 5,360,426 A | 11/1994 | Muller et al. |
| 5,366,456 A | 11/1994 | Rink et al. |
| 5,368,031 A | 11/1994 | Cline et al. |
| 5,368,038 A | 11/1994 | Fraden |
| 5,369,831 A | 12/1994 | Bock |
| 5,370,642 A | 12/1994 | Keller |
| 5,370,649 A | 12/1994 | Gardetto et al. |
| 5,380,317 A | 1/1995 | Everett et al. |
| 5,383,876 A | 1/1995 | Nardella |
| 5,386,427 A | 1/1995 | Zayhowski |
| 5,387,211 A | 2/1995 | Saadatmanesh |
| 5,395,356 A | 3/1995 | King et al. |
| 5,403,306 A | 4/1995 | Edwards et al. |
| 5,405,368 A | 4/1995 | Eckhouse |
| 5,409,446 A | 4/1995 | Rattner |
| 5,409,479 A | 4/1995 | Dew et al. |
| 5,409,481 A | 4/1995 | Poppas et al. |
| 5,415,654 A | 5/1995 | Daikuzono |
| 5,421,337 A | 6/1995 | Richards-Kortum |
| 5,421,339 A | 6/1995 | Ramanujam et al. |
| 5,422,112 A | 6/1995 | Williams |
| 5,423,800 A | 6/1995 | Ren et al. |
| 5,423,803 A | 6/1995 | Tankovich et al. |
| 5,423,805 A | 6/1995 | Brucker et al. |
| 5,425,728 A | 6/1995 | Tankovich |
| 5,425,735 A | 6/1995 | Rosen et al. |
| 5,425,754 A | 6/1995 | Braun et al. |
| 5,439,954 A | 8/1995 | Bush |
| 5,441,499 A | 8/1995 | Fritzsch |
| 5,445,608 A | 8/1995 | Chen et al. |
| 5,445,611 A | 8/1995 | Eppstein et al. |
| 5,454,807 A | 10/1995 | Lennox et al. |
| 5,456,682 A | 10/1995 | Edwards et al. |
| 5,458,140 A | 10/1995 | Eppstein et al. |
| 5,464,436 A | 11/1995 | Smith |
| 5,470,331 A | 11/1995 | Daikuzono |
| 5,472,748 A | 12/1995 | Wolfe et al. |
| 5,474,549 A | 12/1995 | Ortiz et al. |
| 5,484,436 A | 1/1996 | Eggers et al. |
| 5,486,170 A | 1/1996 | Winston et al. |
| 5,486,172 A | 1/1996 | Chess |
| 5,488,626 A | 1/1996 | Heller et al. |
| 5,489,256 A | 2/1996 | Adair |
| 5,492,894 A | 2/1996 | Bascom et al. |
| 5,496,305 A | 3/1996 | Kittrell et al. |
| 5,496,307 A | 3/1996 | Daikuzono |
| 5,498,935 A | 3/1996 | McMahan et al. |
| 5,499,313 A | 3/1996 | Kleinerman |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,507,739 A | 4/1996 | Vassiliadis et al. |
| 5,519,534 A | 5/1996 | Smith |
| 5,521,367 A | 5/1996 | Bard et al. |
| 5,522,813 A | 6/1996 | Trelles |
| 5,527,350 A | 6/1996 | Grove et al. |
| 5,527,368 A | 6/1996 | Supkis et al. |
| 5,530,711 A | 6/1996 | Scheps |
| 5,531,739 A | 7/1996 | Trelles |
| 5,531,740 A | 7/1996 | Black |
| 5,536,168 A | 7/1996 | Bourke et al. |
| 5,540,676 A | 7/1996 | Freiberg |
| 5,540,678 A | 7/1996 | Long et al. |
| 5,540,681 A | 7/1996 | Strul et al. |
| 5,541,948 A | 7/1996 | Krupke et al. |
| 5,546,214 A | 8/1996 | Black et al. |
| 5,549,660 A | 8/1996 | Mendes et al. |
| 5,557,625 A | 9/1996 | Durville |
| 5,558,666 A | 9/1996 | Dewey et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,029 A | 11/1996 | Trelles et al. |
| 5,578,866 A | 11/1996 | DePoorter et al. |
| 5,595,568 A | 1/1997 | Anderson et al. |
| 5,598,426 A | 1/1997 | Hsia et al. |
| 5,608,210 A | 3/1997 | Esparza et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse |
| 5,624,435 A | 4/1997 | Furumoto et al. |
| 5,626,631 A | 5/1997 | Eckhouse |
| 5,628,744 A | 5/1997 | Coleman et al. |
| 5,628,771 A | 5/1997 | Mizukawa et al. |
| 5,630,811 A | 5/1997 | Miller |
| 5,632,741 A | 5/1997 | Zavislan et al. |
| 5,634,711 A | 6/1997 | Kennedy et al. |
| 5,647,866 A | 7/1997 | Zaias et al. |
| 5,649,972 A | 7/1997 | Hochstein |
| 5,651,783 A | 7/1997 | Reynard |
| 5,652,481 A | 7/1997 | Johnson et al. |
| 5,653,706 A | 8/1997 | Zavislan et al. |
| 5,655,547 A | 8/1997 | Karni |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,668,824 A | 9/1997 | Furumoto |
| 5,671,315 A | 9/1997 | Tabuchi et al. |
| 5,673,451 A | 10/1997 | Moore et al. |
| 5,679,113 A | 10/1997 | Caisey et al. |
| 5,683,380 A | 11/1997 | Eckhouse et al. |
| 5,684,902 A | 11/1997 | Tada |
| 5,688,266 A | 11/1997 | Edwards et al. |
| 5,688,267 A | 11/1997 | Panescu et al. |
| 5,692,509 A | 12/1997 | Voss et al. |
| 5,698,866 A | 12/1997 | Doiron et al. |
| 5,707,369 A | 1/1998 | Vaitekunas et al. |
| 5,707,401 A | 1/1998 | Talmore |
| 5,707,403 A | 1/1998 | Grove et al. |
| 5,713,738 A | 2/1998 | Yarborough |
| 5,714,119 A | 2/1998 | Kawagoe et al. |
| 5,720,772 A * | 2/1998 | Eckhouse ............ 607/88 |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,749,868 A | 5/1998 | Furumoto |
| 5,755,751 A | 5/1998 | Eckhouse |
| 5,759,162 A | 6/1998 | Oppelt et al. |
| 5,759,200 A | 6/1998 | Azar |
| 5,760,362 A | 6/1998 | Eloy |
| 5,769,076 A | 6/1998 | Mackawa et al. |
| 5,776,129 A | 7/1998 | Mersch |
| 5,782,249 A | 7/1998 | Weber et al. |
| 5,802,136 A | 9/1998 | Carol |
| 5,807,386 A | 9/1998 | Slatkine et al. |
| 5,810,801 A | 9/1998 | Anderson et al. |
| 5,810,802 A | 9/1998 | Panescu et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |

(56) References Cited

U.S. PATENT DOCUMENTS

| | | |
|---|---|---|
| 5,818,580 A | 10/1998 | Murnick |
| 5,820,625 A | 10/1998 | Izawa et al. |
| 5,820,626 A | 10/1998 | Baumgardner |
| 5,822,034 A | 10/1998 | Shimashita et al. |
| 5,824,023 A | 10/1998 | Anderson |
| 5,827,264 A | 10/1998 | Hohla |
| 5,828,803 A | 10/1998 | Eckhouse |
| 5,830,208 A | 11/1998 | Muller |
| 5,830,209 A | 11/1998 | Savage et al. |
| 5,835,648 A | 11/1998 | Narciso, Jr. et al. |
| 5,836,877 A | 11/1998 | Zavislan |
| 5,836,999 A | 11/1998 | Eckhouse et al. |
| 5,837,001 A | 11/1998 | Mackey |
| 5,840,048 A | 11/1998 | Cheng |
| 5,843,072 A | 12/1998 | Furumoto et al. |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,868,732 A | 2/1999 | Waldman et al. |
| 5,871,479 A | 2/1999 | Furumoto et al. |
| 5,871,480 A | 2/1999 | Tankovich |
| 5,879,159 A | 3/1999 | Cipolla |
| 5,879,346 A | 3/1999 | Waldman et al. |
| 5,879,376 A | 3/1999 | Miller |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,893,885 A | 4/1999 | Webster, Jr. |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,913,833 A | 6/1999 | Elstrom et al. |
| 5,913,883 A | 6/1999 | Alexander et al. |
| 5,916,211 A | 6/1999 | Quon et al. |
| 5,920,374 A | 7/1999 | Vaphiades et al. |
| 5,921,926 A | 7/1999 | Rolland et al. |
| 5,928,222 A | 7/1999 | Kleinerman |
| 5,935,124 A | 8/1999 | Klumb et al. |
| 5,944,687 A | 8/1999 | Benett et al. |
| 5,944,748 A | 8/1999 | Mager et al. |
| 5,948,011 A | 9/1999 | Knowlton |
| 5,949,222 A | 9/1999 | Buono |
| 5,951,543 A | 9/1999 | Brauer |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller |
| 5,968,034 A | 10/1999 | Fullmer et al. |
| 5,971,976 A | 10/1999 | Wang et al. |
| 5,974,059 A | 10/1999 | Dawson |
| 5,974,616 A | 11/1999 | Dreyfus |
| 5,976,123 A | 11/1999 | Baumgardner et al. |
| 5,977,723 A | 11/1999 | Yoon |
| 5,979,454 A * | 11/1999 | Anvari et al. .............. 128/898 |
| 5,983,900 A | 11/1999 | Clement et al. |
| 5,984,915 A | 11/1999 | Loeb et al. |
| 6,007,219 A | 12/1999 | O'Meara |
| 6,015,404 A | 1/2000 | Altshuler et al. |
| 6,022,316 A | 2/2000 | Eppstein et al. |
| 6,022,346 A | 2/2000 | Panescu et al. |
| 6,024,095 A | 2/2000 | Stanley, III |
| 6,026,828 A | 2/2000 | Altshuler |
| 6,027,493 A | 2/2000 | Donitzky et al. |
| 6,027,495 A | 2/2000 | Miller |
| 6,028,694 A | 2/2000 | Schmidt |
| 6,029,303 A | 2/2000 | Dewan |
| 6,029,304 A | 2/2000 | Hulke et al. |
| 6,030,378 A | 2/2000 | Stewart |
| 6,030,399 A | 2/2000 | Ignotz et al. |
| 6,032,071 A | 2/2000 | Binder |
| RE36,634 E | 3/2000 | Ghaffari |
| 6,033,431 A | 3/2000 | Segal |
| 6,036,684 A | 3/2000 | Tankovich et al. |
| 6,044,514 A | 4/2000 | Kaneda et al. |
| 6,045,548 A | 4/2000 | Furumoto et al. |
| 6,050,990 A | 4/2000 | Tankovich et al. |
| D424,197 S | 5/2000 | Sydlowski et al. |
| 6,056,548 A | 5/2000 | Neuberger et al. |
| 6,056,738 A | 5/2000 | Marchitto et al. |
| 6,058,937 A | 5/2000 | Doiron et al. |
| 6,059,820 A | 5/2000 | Baronov |
| 6,063,108 A | 5/2000 | Salansky et al. |
| 6,070,092 A | 5/2000 | Kazama et al. |
| 6,071,239 A | 6/2000 | Cribbs et al. |
| 6,074,382 A | 6/2000 | Asah et al. |
| 6,077,294 A | 6/2000 | Cho et al. |
| 6,080,146 A | 6/2000 | Altshuler et al. |
| 6,080,147 A | 6/2000 | Tobinick |
| 6,083,217 A | 7/2000 | Tankovich |
| 6,086,363 A | 7/2000 | Moran et al. |
| 6,086,558 A | 7/2000 | Bower et al. |
| 6,086,580 A | 7/2000 | Mordon et al. |
| 6,094,767 A | 8/2000 | Iimura |
| 6,096,028 A | 8/2000 | Bahmanyar et al. |
| 6,096,029 A | 8/2000 | O'Donnell, Jr. |
| 6,096,209 A | 8/2000 | O'Brien et al. |
| 6,099,521 A | 8/2000 | Shadduck |
| 6,101,207 A | 8/2000 | Ilorinne |
| 6,104,959 A | 8/2000 | Spertell |
| 6,106,293 A | 8/2000 | Wiesel |
| 6,106,294 A | 8/2000 | Daniel |
| 6,110,195 A | 8/2000 | Xie et al. |
| 6,112,123 A | 8/2000 | Kelleher et al. |
| 6,113,559 A | 9/2000 | Klopotek |
| 6,117,129 A | 9/2000 | Mukai |
| 6,120,497 A | 9/2000 | Anderson |
| 6,126,655 A | 10/2000 | Domankevitz et al. |
| 6,129,723 A | 10/2000 | Anderson et al. |
| 6,135,774 A | 10/2000 | Hack et al. |
| 6,142,650 A | 11/2000 | Brown et al. |
| 6,142,939 A | 11/2000 | Eppstein et al. |
| 6,149,644 A | 11/2000 | Xie |
| 6,149,895 A | 11/2000 | Kutsch |
| 6,159,203 A | 12/2000 | Sinofsky et al. |
| 6,159,236 A | 12/2000 | Biel |
| 6,162,055 A | 12/2000 | Montgomery et al. |
| 6,162,211 A * | 12/2000 | Tankovich et al. .............. 606/9 |
| 6,162,212 A | 12/2000 | Kreindel et al. |
| 6,162,215 A | 12/2000 | Feng |
| 6,162,218 A | 12/2000 | Elbrecht et al. |
| 6,164,837 A | 12/2000 | Haake et al. |
| 6,171,300 B1 | 1/2001 | Adams |
| 6,171,301 B1 | 1/2001 | Nelson |
| 6,171,302 B1 | 1/2001 | Talpalriu et al. |
| 6,171,332 B1 | 1/2001 | Whitehurst |
| 6,173,202 B1 | 1/2001 | Eppstein et al. |
| 6,174,325 B1 | 1/2001 | Eckhouse |
| 6,176,854 B1 | 1/2001 | Cone |
| 6,183,434 B1 | 2/2001 | Eppstein |
| 6,183,500 B1 | 2/2001 | Kohler |
| 6,183,773 B1 | 2/2001 | Anderson |
| 6,187,001 B1 | 2/2001 | Azar et al. |
| 6,187,029 B1 | 2/2001 | Shapiro et al. |
| 6,197,020 B1 | 3/2001 | O'Donnell |
| 6,200,134 B1 | 3/2001 | Kovac et al. |
| 6,200,309 B1 | 3/2001 | Rice et al. |
| 6,202,242 B1 | 3/2001 | Salmon et al. |
| 6,203,540 B1 | 3/2001 | Weber |
| 6,210,425 B1 | 4/2001 | Chen |
| 6,210,426 B1 | 4/2001 | Cho et al. |
| 6,214,034 B1 | 4/2001 | Azar |
| 6,221,068 B1 | 4/2001 | Fried et al. |
| 6,221,095 B1 | 4/2001 | Van Zuylen et al. |
| 6,228,074 B1 | 5/2001 | Almeida |
| 6,228,075 B1 | 5/2001 | Furumoto |
| 6,229,831 B1 | 5/2001 | Nightingale et al. |
| 6,230,044 | 5/2001 | Afanassieva et al. |

(56) References Cited

U.S. PATENT DOCUMENTS

| | | |
|---|---|---|
| 6,235,015 B1 | 5/2001 | Mead, III et al. |
| 6,235,016 B1 | 5/2001 | Stewart |
| 6,236,891 B1 | 5/2001 | Ingel et al. |
| 6,239,442 B1 | 5/2001 | Iimura et al. |
| 6,240,306 B1 | 5/2001 | Rohrscheib et al. |
| 6,240,925 B1 | 6/2001 | McMillan et al. |
| 6,245,093 B1 | 6/2001 | Li et al. |
| 6,246,710 B1 | 6/2001 | Furumoto |
| 6,248,103 B1 | 6/2001 | Tannenbaum et al. |
| 6,251,127 B1 | 6/2001 | Biel |
| 6,254,388 B1 | 7/2001 | Yarborough |
| 6,263,233 B1 | 7/2001 | Zavislan et al. |
| 6,264,649 B1 | 7/2001 | Whitcroft et al. |
| 6,267,779 B1 | 7/2001 | Gerdes |
| 6,267,780 B1 | 7/2001 | Streeter |
| 6,273,883 B1 | 8/2001 | Furumoto |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,282,442 B1 | 8/2001 | Destefano et al. |
| 6,283,956 B1 | 9/2001 | McDaniel |
| 6,287,549 B1 | 9/2001 | Sumian et al. |
| 6,290,496 B1 | 9/2001 | Azar et al. |
| 6,290,712 B1 | 9/2001 | Nordquist et al. |
| 6,290,713 B1 | 9/2001 | Russell |
| 6,306,130 B1 | 10/2001 | Anderson et al. |
| 6,306,160 B1 | 10/2001 | Nidetzky |
| 6,315,772 B1 | 11/2001 | Marchitto et al. |
| 6,317,624 B1 | 11/2001 | Kollias et al. |
| 6,319,274 B1 | 11/2001 | Shadduck |
| 6,322,584 B2 | 11/2001 | Ingle et al. |
| 6,325,769 B1 | 12/2001 | Klopotek |
| 6,327,506 B1 | 12/2001 | Yogo et al. |
| 6,328,733 B1 | 12/2001 | Trost |
| 6,331,111 B1 | 12/2001 | Cao |
| 6,332,891 B1 | 12/2001 | Himes |
| 6,338,855 B1 | 1/2002 | Albacarys et al. |
| 6,340,495 B1 | 1/2002 | Sumian et al. |
| 6,343,400 B1 | 2/2002 | Massholder et al. |
| 6,343,933 B1 | 2/2002 | Montgomery et al. |
| 6,350,261 B1 | 2/2002 | Domankevitz et al. |
| 6,350,276 B1 | 2/2002 | Knowlton |
| 6,354,370 B1 | 3/2002 | Miller et al. |
| 6,355,054 B1 | 3/2002 | Neuberger et al. |
| 6,358,242 B1 | 3/2002 | Cecchetti |
| 6,358,272 B1 | 3/2002 | Wilden |
| 6,364,872 B1 | 4/2002 | Hsia et al. |
| 6,383,176 B1 | 5/2002 | Connors et al. |
| 6,383,177 B1 | 5/2002 | Balle-Petersen et al. |
| 6,387,089 B1 | 5/2002 | Kreindel et al. |
| 6,387,353 B1 | 5/2002 | Jensen et al. |
| 6,391,022 B1 | 5/2002 | Furumoto et al. |
| 6,394,949 B1 | 5/2002 | Crowley et al. |
| 6,395,016 B1 | 5/2002 | Oron et al. |
| 6,398,801 B1 | 6/2002 | Clement et al. |
| 6,400,011 B1 | 6/2002 | Miki |
| 6,402,739 B1 | 6/2002 | Neev |
| 6,405,732 B1 | 6/2002 | Edwards et al. |
| 6,406,474 B1 | 6/2002 | Neuberger et al. |
| 6,409,665 B1 | 6/2002 | Scott et al. |
| 6,409,723 B1 | 6/2002 | Edwards |
| 6,413,267 B1 | 7/2002 | Dumoulin-White et al. |
| 6,416,319 B1 | 7/2002 | Cipolla |
| 6,419,389 B1 | 7/2002 | Fuchs et al. |
| 6,424,852 B1 | 7/2002 | Zavislan |
| 6,425,912 B1 | 7/2002 | Knowlton |
| 6,435,873 B1 | 8/2002 | Burgio |
| 6,436,094 B1 | 8/2002 | Reuter |
| 6,439,888 B1 | 8/2002 | Boutoussov et al. |
| 6,440,155 B1 | 8/2002 | Matsumae et al. |
| 6,443,946 B2 | 9/2002 | Clement et al. |
| 6,443,978 B1 | 9/2002 | Zharov et al. |
| 6,447,503 B1 | 9/2002 | Wynne et al. |
| 6,447,504 B1 | 9/2002 | Ben-Haim et al. |
| 6,451,007 B1 | 9/2002 | Koop et al. |
| 6,454,790 B1 | 9/2002 | Neuberger et al. |
| 6,459,919 B1 | 10/2002 | Lys et al. |
| 6,461,296 B1 | 10/2002 | Desai |
| 6,464,694 B1 | 10/2002 | Massengill |
| 6,470,216 B1 | 10/2002 | Knowlton |
| 6,471,712 B2 | 10/2002 | Burres |
| 6,471,716 B1 | 10/2002 | Pecukonis |
| 6,475,211 B2 * | 11/2002 | Chess et al. ................ 606/9 |
| 6,484,052 B1 | 11/2002 | Visuri et al. |
| 6,485,413 B1 | 11/2002 | Boppart et al. |
| 6,491,685 B2 | 12/2002 | Visuri et al. |
| 6,491,715 B1 | 12/2002 | Abels et al. |
| 6,493,608 B1 | 12/2002 | Niemeyer |
| 6,494,900 B1 | 12/2002 | Salansky et al. |
| 6,497,702 B1 | 12/2002 | Bernaz |
| 6,503,269 B2 | 1/2003 | Nield et al. |
| 6,503,486 B2 | 1/2003 | Xu et al. |
| 6,508,785 B1 | 1/2003 | Eppstein |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,517,532 B1 | 2/2003 | Altshuler et al. |
| 6,519,376 B2 | 2/2003 | Biagi et al. |
| 6,525,819 B1 | 2/2003 | Delawter et al. |
| 6,527,716 B1 | 3/2003 | Eppstein |
| 6,527,764 B1 | 3/2003 | Neuberger et al. |
| 6,529,540 B1 | 3/2003 | Demmer et al. |
| 6,530,915 B1 | 3/2003 | Eppstein et al. |
| 6,530,916 B1 | 3/2003 | Shimmick |
| 6,537,270 B1 | 3/2003 | Elbrecht et al. |
| 6,544,257 B2 | 4/2003 | Nagase et al. |
| 6,547,780 B1 | 4/2003 | Sinofsky |
| 6,551,346 B2 | 4/2003 | Crossley |
| 6,554,439 B1 | 4/2003 | Teicher et al. |
| 6,556,596 B1 | 4/2003 | Kim et al. |
| 6,558,372 B1 | 5/2003 | Altshuler |
| 6,561,808 B2 | 5/2003 | Neuberger et al. |
| 6,569,155 B1 | 5/2003 | Connors et al. |
| 6,570,892 B1 | 5/2003 | Lin et al. |
| 6,570,893 B1 | 5/2003 | Libatique et al. |
| 6,572,634 B2 | 6/2003 | Koo |
| 6,572,637 B1 | 6/2003 | Yamazaki et al. |
| 6,595,934 B1 | 7/2003 | Hissong et al. |
| 6,600,951 B1 | 7/2003 | Anderson |
| 6,602,245 B1 | 8/2003 | Thiberg |
| 6,602,275 B1 | 8/2003 | Sullivan |
| 6,603,988 B2 | 8/2003 | Dowlatshahi |
| 6,605,080 B1 * | 8/2003 | Altshuler et al. ............ 606/3 |
| 6,605,083 B1 | 8/2003 | Clement et al. |
| 6,606,755 B1 | 8/2003 | Robinson et al. |
| 6,607,525 B2 | 8/2003 | France et al. |
| 6,610,052 B2 | 8/2003 | Furumoto |
| 6,613,040 B2 | 9/2003 | Tankovich et al. |
| 6,616,447 B1 | 9/2003 | Rizoiu et al. |
| 6,616,451 B1 | 9/2003 | Rizolu et al. |
| 6,618,531 B1 | 9/2003 | Goto et al. |
| 6,623,272 B2 | 9/2003 | Clemans |
| 6,623,513 B2 | 9/2003 | Biel |
| 6,629,971 B2 | 10/2003 | McDaniel |
| 6,629,989 B2 | 10/2003 | Akita |
| 6,632,219 B1 | 10/2003 | Baranov et al. |
| 6,635,075 B2 | 10/2003 | Li et al. |
| 6,641,578 B2 | 11/2003 | Mukai |
| 6,641,600 B1 | 11/2003 | Kohler |
| 6,648,904 B2 | 11/2003 | Altshuler et al. |
| 6,652,459 B2 | 11/2003 | Payne et al. |
| 6,653,618 B2 | 11/2003 | Zenzie |
| 6,659,999 B1 | 12/2003 | Anderson et al. |
| 6,660,000 B2 | 12/2003 | Neuberger et al. |
| 6,663,620 B2 | 12/2003 | Altshuler et al. |
| 6,663,658 B1 | 12/2003 | Kollias et al. |
| 6,663,659 B2 | 12/2003 | McDaniel |
| 6,666,856 B2 * | 12/2003 | Connors et al. ............... 606/9 |
| 6,669,685 B1 | 12/2003 | Rizoiu et al. |
| 6,675,425 B1 | 1/2004 | Iimura et al. |
| 6,676,654 B1 | 1/2004 | Balle-Petersen et al. |
| 6,679,837 B2 | 1/2004 | Daikuzono |
| 6,682,523 B2 | 1/2004 | Shadduck |
| 6,682,524 B1 | 1/2004 | Elbrecht et al. |

(56) References Cited

U.S. PATENT DOCUMENTS

| | | |
|---|---|---|
| 6,685,639 B1 | 2/2004 | Wang et al. |
| 6,685,699 B1 | 2/2004 | Eppstein et al. |
| 6,685,722 B1 | 2/2004 | Rosenbluth et al. |
| 6,689,124 B1 | 2/2004 | Thiberg |
| 6,692,456 B1 | 2/2004 | Eppstein et al. |
| 6,692,517 B2 | 2/2004 | Cho et al. |
| 6,699,040 B1 | 3/2004 | Hahn et al. |
| 6,706,035 B2 | 3/2004 | Cense et al. |
| 6,709,269 B1 | 3/2004 | Altshuler |
| 6,709,446 B2 | 3/2004 | Lundahl et al. |
| 6,723,090 B2 | 4/2004 | Altshuler et al. |
| 6,724,958 B1 | 4/2004 | German et al. |
| 6,726,681 B2 | 4/2004 | Grasso et al. |
| 6,736,807 B2 | 5/2004 | Yamazaki et al. |
| 6,743,222 B2 | 6/2004 | Durkin et al. |
| 6,746,444 B2 | 6/2004 | Key |
| 6,749,623 B1 | 6/2004 | Hsi et al. |
| 6,755,647 B2 | 6/2004 | Melikechi et al. |
| 6,770,069 B1 | 8/2004 | Hobart et al. |
| 6,772,053 B2 | 8/2004 | Niemeyer |
| 6,790,205 B1 | 9/2004 | Yamazaki et al. |
| 6,801,595 B2 | 10/2004 | Grodzins et al. |
| 6,808,331 B2 | 10/2004 | Hall et al. |
| 6,808,532 B2 | 10/2004 | Anderson et al. |
| 6,824,542 B2 | 11/2004 | Jay |
| RE38,670 E | 12/2004 | Asah et al. |
| 6,858,009 B2 | 2/2005 | Kawata et al. |
| 6,860,879 B2 | 3/2005 | Irion et al. |
| 6,860,896 B2 | 3/2005 | Leber et al. |
| 6,862,771 B1 | 3/2005 | Muller |
| 6,863,781 B2 * | 3/2005 | Nocera et al. .......... 204/157.52 |
| 6,872,203 B2 | 3/2005 | Shafirstein et al. |
| 6,878,144 B2 | 4/2005 | Altshuler et al. |
| 6,881,212 B1 | 4/2005 | Clement et al. |
| 6,887,260 B1 | 5/2005 | McDaniel |
| 6,888,319 B2 | 5/2005 | Inochkin et al. |
| 6,893,259 B1 | 5/2005 | Reizenson |
| 6,902,397 B2 | 6/2005 | Farrell et al. |
| 6,902,563 B2 | 6/2005 | Wilkens et al. |
| 6,905,492 B2 | 6/2005 | Zvuloni et al. |
| 6,916,316 B2 | 7/2005 | Jay |
| 6,936,046 B2 | 8/2005 | Hissong et al. |
| 6,942,658 B1 | 9/2005 | Rizoiu et al. |
| 6,953,341 B2 | 10/2005 | Black |
| 6,974,450 B2 | 12/2005 | Weber et al. |
| 6,974,451 B2 | 12/2005 | Altshuler et al. |
| 6,976,985 B2 | 12/2005 | Altshuler et al. |
| 6,986,903 B2 | 1/2006 | Zulli et al. |
| 6,989,007 B2 | 1/2006 | Shadduck |
| 6,989,023 B2 | 1/2006 | Black |
| 6,991,644 B2 | 1/2006 | Spooner et al. |
| 6,997,923 B2 | 2/2006 | Anderson et al. |
| 7,001,413 B2 | 2/2006 | Butler |
| 7,006,223 B2 | 2/2006 | Mullani |
| 7,018,396 B2 | 3/2006 | Sierra et al. |
| 7,029,469 B2 | 4/2006 | Vasily |
| 7,033,349 B2 | 4/2006 | Key |
| 7,041,094 B2 | 5/2006 | Connors et al. |
| 7,041,100 B2 | 5/2006 | Kreindel |
| 7,044,959 B2 | 5/2006 | Anderson et al. |
| 7,060,061 B2 | 6/2006 | Altshuler et al. |
| 7,066,733 B2 | 6/2006 | Logan et al. |
| 7,070,611 B2 | 7/2006 | Biel |
| 7,077,840 B2 | 7/2006 | Altshuler et al. |
| 7,081,128 B2 | 7/2006 | Hart et al. |
| 7,097,639 B1 | 8/2006 | Almeida |
| 7,097,656 B1 | 8/2006 | Akopov et al. |
| 7,104,985 B2 | 9/2006 | Martinelli |
| 7,118,562 B2 | 10/2006 | Furumoto |
| 7,118,563 B2 | 10/2006 | Weckwerth et al. |
| 7,135,033 B2 | 11/2006 | Altshuler et al. |
| 7,144,247 B2 | 12/2006 | Black |
| 7,144,248 B2 | 12/2006 | Irwin |
| 7,145,105 B2 | 12/2006 | Gaulard |
| 7,145,108 B2 | 12/2006 | Kanel et al. |
| 7,160,289 B2 | 1/2007 | Cohen |
| 7,170,034 B2 | 1/2007 | Shalev |
| 7,175,617 B2 | 2/2007 | Jay |
| 7,182,760 B2 | 2/2007 | Kubota |
| 7,198,634 B2 | 4/2007 | Harth et al. |
| 7,202,446 B2 | 4/2007 | Shalev |
| 7,204,832 B2 | 4/2007 | Altshuler et al. |
| 7,216,055 B1 | 5/2007 | Horton et al. |
| 7,217,265 B2 | 5/2007 | Hennings et al. |
| 7,217,267 B2 | 5/2007 | Jay |
| 7,220,254 B2 | 5/2007 | Altshuler et al. |
| 7,223,270 B2 | 5/2007 | Altshuler et al. |
| 7,223,281 B2 | 5/2007 | Altshuler et al. |
| 7,255,691 B2 | 8/2007 | Tolkoff et al. |
| 7,274,155 B2 | 9/2007 | Inochkin et al. |
| 7,276,058 B2 | 10/2007 | Altshuler et al. |
| 7,280,866 B1 | 10/2007 | McIntosh et al. |
| 7,282,060 B2 | 10/2007 | DeBenedictis |
| 7,282,723 B2 | 10/2007 | Schomaket et al. |
| 7,291,140 B2 | 11/2007 | MacFarland et al. |
| 7,291,141 B2 | 11/2007 | Jay |
| 7,309,335 B2 | 12/2007 | Altshuler et al. |
| 7,311,722 B2 | 12/2007 | Larsen |
| 7,322,972 B2 | 1/2008 | Viator et al. |
| 7,329,273 B2 | 2/2008 | Altshuler et al. |
| 7,329,274 B2 | 2/2008 | Altshuler et al. |
| 7,331,953 B2 | 2/2008 | Manstein et al. |
| 7,331,964 B2 | 2/2008 | Maricle et al. |
| 7,333,698 B2 | 2/2008 | Israel |
| 7,351,252 B2 * | 4/2008 | Altshuler et al. .............. 607/88 |
| 7,354,448 B2 | 4/2008 | Altshuler et al. |
| 7,422,598 B2 | 9/2008 | Altshuler et al. |
| 7,423,767 B2 | 9/2008 | Steinsiek et al. |
| 7,431,419 B2 | 10/2008 | Turner et al. |
| 7,431,719 B2 | 10/2008 | Altshuler et al. |
| 7,436,863 B2 | 10/2008 | Matsuda et al. |
| 7,500,956 B1 | 3/2009 | Wilk |
| 7,531,967 B2 | 5/2009 | Inochkin et al. |
| 7,540,869 B2 | 6/2009 | Altshuler et al. |
| 7,553,308 B2 | 6/2009 | Jay |
| 7,588,547 B2 | 9/2009 | Deem et al. |
| 7,624,640 B2 | 12/2009 | Maris et al. |
| 7,647,092 B2 | 1/2010 | Motz et al. |
| 7,699,058 B1 | 4/2010 | Jay |
| 7,722,600 B2 | 5/2010 | Connors et al. |
| 7,758,621 B2 | 7/2010 | Altshuler et al. |
| 7,763,016 B2 | 7/2010 | Altshuler et al. |
| 7,839,972 B2 | 11/2010 | Ruchala et al. |
| 7,856,985 B2 | 12/2010 | Mirkov et al. |
| 7,931,028 B2 | 4/2011 | Jay |
| 7,935,107 B2 | 5/2011 | Altshuler et al. |
| 7,938,821 B2 | 5/2011 | Chan et al. |
| 7,942,869 B2 | 5/2011 | Houbolt et al. |
| 7,942,915 B2 | 5/2011 | Altshuler et al. |
| 7,942,916 B2 | 5/2011 | Altshuler et al. |
| 7,998,181 B2 | 8/2011 | Nightingale et al. |
| 8,002,768 B1 | 8/2011 | Altshuler et al. |
| 8,027,710 B1 | 9/2011 | Dannan |
| 8,109,924 B2 | 2/2012 | Altshuler |
| 8,182,473 B2 | 5/2012 | Altshuler et al. |
| 8,328,794 B2 | 12/2012 | Altshuler et al. |
| 8,328,796 B2 | 12/2012 | Altshuler et al. |
| 8,378,322 B2 | 2/2013 | Dahm et al. |
| 2001/0007068 A1 | 7/2001 | Ota et al. |
| 2001/0008973 A1 | 7/2001 | Van Zuylen et al. |
| 2001/0016732 A1 | 8/2001 | Hobart et al. |
| 2001/0023363 A1 | 9/2001 | Harth et al. |
| 2001/0024777 A1 | 9/2001 | Azar et al. |
| 2001/0025173 A1 | 9/2001 | Ritchie et al. |
| 2001/0029956 A1 | 10/2001 | Argenta et al. |
| 2001/0041886 A1 | 11/2001 | Durkin et al. |
| 2001/0046652 A1 | 11/2001 | Ostler et al. |
| 2001/0048077 A1 | 12/2001 | Afanassieva |
| 2002/0002367 A1 | 1/2002 | Tankovich et al. |
| 2002/0004066 A1 | 1/2002 | Stanley et al. |
| 2002/0005475 A1 | 1/2002 | Zenzie |
| 2002/0013572 A1 | 1/2002 | Berlin |
| 2002/0016587 A1 | 2/2002 | Furumoto |
| 2002/0018754 A1 | 2/2002 | Sagel et al. |

(56) References Cited

U.S. PATENT DOCUMENTS

| | | |
|---|---|---|
| 2002/0019624 A1 | 2/2002 | Clement |
| 2002/0019625 A1 | 2/2002 | Azar |
| 2002/0026225 A1 | 2/2002 | Segal |
| 2002/0029071 A1 | 3/2002 | Whitehurst |
| 2002/0032437 A1 | 3/2002 | Andrews et al. |
| 2002/0045891 A1 | 4/2002 | Clement et al. |
| 2002/0049432 A1 | 4/2002 | Mukai |
| 2002/0049483 A1 | 4/2002 | Knowlton |
| 2002/0058890 A1 | 5/2002 | Visuri et al. |
| 2002/0071287 A1 | 6/2002 | Haase |
| 2002/0071827 A1 | 6/2002 | Petersen et al. |
| 2002/0072676 A1 | 6/2002 | Afanassieva |
| 2002/0081555 A1 | 6/2002 | Wiesel |
| 2002/0090725 A1 | 7/2002 | Simpson et al. |
| 2002/0091377 A1 | 7/2002 | Anderson |
| 2002/0108193 A1 | 8/2002 | Gruber |
| 2002/0111610 A1 | 8/2002 | Nordquist |
| 2002/0120256 A1 | 8/2002 | Furuno et al. |
| 2002/0123745 A1 | 9/2002 | Svaasand et al. |
| 2002/0127224 A1 | 9/2002 | Chen |
| 2002/0128635 A1 | 9/2002 | Altshuler et al. |
| 2002/0128695 A1 | 9/2002 | Harth et al. |
| 2002/0128696 A1 | 9/2002 | Pearl |
| 2002/0151878 A1 | 10/2002 | Shimmick et al. |
| 2002/0151879 A1 | 10/2002 | Loeb |
| 2002/0161357 A1 | 10/2002 | Anderson |
| 2002/0161418 A1 | 10/2002 | Wilkens et al. |
| 2002/0167974 A1 | 11/2002 | Kennedy et al. |
| 2002/0173723 A1 | 11/2002 | Lewis |
| 2002/0173777 A1 | 11/2002 | Sand |
| 2002/0173780 A1 | 11/2002 | Altshuler et al. |
| 2002/0173781 A1 | 11/2002 | Cense et al. |
| 2002/0182563 A1 | 12/2002 | Boutoussov et al. |
| 2002/0183808 A1 | 12/2002 | Biel |
| 2002/0198517 A1 | 12/2002 | Alfano et al. |
| 2003/0004499 A1 | 1/2003 | McDaniel |
| 2003/0009158 A1 | 1/2003 | Perricone |
| 2003/0009205 A1 | 1/2003 | Biel |
| 2003/0018373 A1 | 1/2003 | Eckhardt et al. |
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028186 A1 | 2/2003 | Kreintel |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055413 A1 | 3/2003 | Altshuler et al. |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0073989 A1 | 4/2003 | Hoey et al. |
| 2003/0083649 A1 | 5/2003 | Margaron et al. |
| 2003/0084534 A1 | 5/2003 | Kaizuka |
| 2003/0092982 A1 | 5/2003 | Eppstein |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0158550 A1 | 8/2003 | Ganz et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187319 A1 | 10/2003 | Kaneko |
| 2003/0187383 A1 | 10/2003 | Weber et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216719 A1 | 11/2003 | Debenedictis et al. |
| 2003/0216795 A1 | 11/2003 | Harth et al. |
| 2003/0232303 A1 | 12/2003 | Black |
| 2003/0233138 A1 | 12/2003 | Spooner |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019120 A1 | 1/2004 | Vargas et al. |
| 2004/0019990 A1 | 2/2004 | Farrell et al. |
| 2004/0024388 A1 | 2/2004 | Altshuler |
| 2004/0024430 A1 | 2/2004 | Bader et al. |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0036975 A1 | 2/2004 | Slatkine |
| 2004/0054248 A1 | 3/2004 | Kimchy et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0092506 A1 | 5/2004 | Thompson et al. |
| 2004/0093042 A1 | 5/2004 | Altshuler et al. |
| 2004/0093043 A1 | 5/2004 | Edel et al. |
| 2004/0098070 A1 | 5/2004 | Mohr et al. |
| 2004/0105611 A1 | 6/2004 | Bischel et al. |
| 2004/0111086 A1 | 6/2004 | Trombly |
| 2004/0111132 A1 | 6/2004 | Shenderova et al. |
| 2004/0116984 A1 | 6/2004 | Spooner et al. |
| 2004/0122311 A1 | 6/2004 | Cosman |
| 2004/0133251 A1 | 7/2004 | Altshuler et al. |
| 2004/0143181 A1 | 7/2004 | Damasio et al. |
| 2004/0143247 A1 | 7/2004 | Anderson et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162490 A1 | 8/2004 | Soltz et al. |
| 2004/0162549 A1 | 8/2004 | Altshuler et al. |
| 2004/0162596 A1 | 8/2004 | Altshuler et al. |
| 2004/0167502 A1 | 8/2004 | Weckwerth et al. |
| 2004/0176754 A1 | 9/2004 | Island et al. |
| 2004/0186465 A1 | 9/2004 | Francischelli |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199079 A1 | 10/2004 | Chuck et al. |
| 2004/0199151 A1 | 10/2004 | Neuberger |
| 2004/0199227 A1 | 10/2004 | Altshuler et al. |
| 2004/0204745 A1 | 10/2004 | Altshuler et al. |
| 2004/0208918 A1 | 10/2004 | Koch et al. |
| 2004/0210275 A1 | 10/2004 | Town et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2004/0249261 A1 | 12/2004 | Torchia et al. |
| 2004/0260210 A1 | 12/2004 | Ella et al. |
| 2005/0015077 A1 | 1/2005 | Kuklin et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065502 A1 | 3/2005 | Stoltz |
| 2005/0065531 A1 | 3/2005 | Cohen |
| 2005/0074038 A1 | 4/2005 | Khaydarov |
| 2005/0080404 A1 | 4/2005 | Jones et al. |
| 2005/0085875 A1 | 4/2005 | Van Zuylen |
| 2005/0102213 A1 | 5/2005 | Savasoglu et al. |
| 2005/0107849 A1 | 5/2005 | Altshuler et al. |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143719 A1 | 6/2005 | Sink |

(56) References Cited

U.S. PATENT DOCUMENTS

| | | |
|---|---|---|
| 2005/0143723 A1 | 6/2005 | Zvuloni et al. |
| 2005/0154380 A1 | 7/2005 | DeBenedictis |
| 2005/0165315 A1 | 7/2005 | Zuluga et al. |
| 2005/0165393 A1 | 7/2005 | Eppstein |
| 2005/0168158 A1 | 8/2005 | Inochkin et al. |
| 2005/0170313 A1 | 8/2005 | Pitz et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0177139 A1 | 8/2005 | Yamazaki et al. |
| 2005/0177142 A1 | 8/2005 | Jay |
| 2005/0182389 A1 | 8/2005 | LaPorte et al. |
| 2005/0197681 A1 | 9/2005 | Barolet et al. |
| 2005/0203496 A1 | 9/2005 | Ritchie et al. |
| 2005/0203497 A1 | 9/2005 | Speeg et al. |
| 2005/0215988 A1 | 9/2005 | Altshuler et al. |
| 2005/0220726 A1 | 10/2005 | Pauly et al. |
| 2005/0222556 A1 | 10/2005 | Arivra et al. |
| 2005/0245917 A1 | 11/2005 | Strassl et al. |
| 2005/0251116 A1 | 11/2005 | Steinke et al. |
| 2005/0251117 A1 | 11/2005 | Anderson et al. |
| 2005/0251118 A1 | 11/2005 | Anderson et al. |
| 2005/0257612 A1 | 11/2005 | Hiemer et al. |
| 2005/0281530 A1 | 12/2005 | Rizoiu et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0009750 A1 | 1/2006 | Altshuler et al. |
| 2006/0013533 A1 | 1/2006 | Slatkine |
| 2006/0020309 A1 | 1/2006 | Altshuler et al. |
| 2006/0047281 A1 | 3/2006 | Kreindel |
| 2006/0052661 A1 | 3/2006 | Gannot et al. |
| 2006/0056589 A1 | 3/2006 | Engelward |
| 2006/0058712 A1 | 3/2006 | Altshuler et al. |
| 2006/0062448 A1 | 3/2006 | Hirsch et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0100677 A1 | 5/2006 | Blumenkranz et al. |
| 2006/0116671 A1 | 6/2006 | Slayton et al. |
| 2006/0118127 A1 | 6/2006 | Chinn |
| 2006/0122584 A1 | 6/2006 | Bommannan et al. |
| 2006/0122668 A1 | 6/2006 | Anderson et al. |
| 2006/0128771 A1 | 6/2006 | Mirkov et al. |
| 2006/0149343 A1 | 7/2006 | Altshuler et al. |
| 2006/0155266 A1 | 7/2006 | Manstein et al. |
| 2006/0161143 A1 | 7/2006 | Altshuler et al. |
| 2006/0173480 A1 | 8/2006 | Zhang |
| 2006/0194164 A1 | 8/2006 | Altshuler et al. |
| 2006/0206103 A1 | 9/2006 | Altshuler et al. |
| 2006/0217689 A1 | 9/2006 | Dick et al. |
| 2006/0224148 A1 | 10/2006 | Chou et al. |
| 2006/0247609 A1 | 11/2006 | Mirkov et al. |
| 2006/0253176 A1 | 11/2006 | Caruso et al. |
| 2006/0259102 A1 | 11/2006 | Slatkine |
| 2006/0265032 A1 | 11/2006 | Hennings |
| 2006/0271028 A1 | 11/2006 | Altshuler et al. |
| 2006/0282067 A1* | 12/2006 | Koop et al. ............... 606/9 |
| 2006/0287646 A1 | 12/2006 | Altshuler et al. |
| 2006/0293727 A1 | 12/2006 | Spooner et al. |
| 2006/0293728 A1 | 12/2006 | Roersma et al. |
| 2007/0027440 A1 | 2/2007 | Altshuler et al. |
| 2007/0038206 A1 | 2/2007 | Altshuler et al. |
| 2007/0038271 A1 | 2/2007 | Cole et al. |
| 2007/0049910 A1 | 3/2007 | Altshuler et al. |
| 2007/0060819 A1 | 3/2007 | Altshuler et al. |
| 2007/0060989 A1 | 3/2007 | Deem et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0088206 A1 | 4/2007 | Peyman |
| 2007/0093797 A1 | 4/2007 | Chan et al. |
| 2007/0105212 A1 | 5/2007 | Oldham et al. |
| 2007/0121069 A1 | 5/2007 | Andersen et al. |
| 2007/0123851 A1 | 5/2007 | Alejandro et al. |
| 2007/0142881 A1 | 6/2007 | Hennings |
| 2007/0159592 A1 | 7/2007 | Rylander et al. |
| 2007/0173749 A1 | 7/2007 | Williams et al. |
| 2007/0179378 A1 | 8/2007 | Boese et al. |
| 2007/0179470 A1 | 8/2007 | Toombs |
| 2007/0185552 A1 | 8/2007 | Masotti et al. |
| 2007/0194717 A1 | 8/2007 | Belikov et al. |
| 2007/0198004 A1 | 8/2007 | Altshuler et al. |
| 2007/0208252 A1 | 9/2007 | Makower |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219602 A1 | 9/2007 | Ostrovsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0244527 A1 | 10/2007 | Hatayama et al. |
| 2007/0255355 A1 | 11/2007 | Altshuler et al. |
| 2007/0260230 A1 | 11/2007 | Youngquist et al. |
| 2007/0264625 A1 | 11/2007 | DeBenedictis |
| 2007/0288071 A1 | 12/2007 | Rogers |
| 2008/0003536 A1 | 1/2008 | Altshuler et al. |
| 2008/0004608 A1 | 1/2008 | Dacquay et al. |
| 2008/0004611 A1 | 1/2008 | Houbolt et al. |
| 2008/0009842 A1 | 1/2008 | Manstein et al. |
| 2008/0033516 A1 | 2/2008 | Altshuler et al. |
| 2008/0058782 A1 | 3/2008 | Frangineas et al. |
| 2008/0058783 A1 | 3/2008 | Altshuler et al. |
| 2008/0103565 A1 | 5/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0147054 A1 | 6/2008 | Altshuler et al. |
| 2008/0154157 A1 | 6/2008 | Altshuler et al. |
| 2008/0154247 A1 | 6/2008 | Dallarosa |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0186591 A1 | 8/2008 | Altshuler et al. |
| 2008/0194969 A1 | 8/2008 | Werahera et al. |
| 2008/0195183 A1 | 8/2008 | Botchkareva et al. |
| 2008/0208105 A1 | 8/2008 | Zelickson et al. |
| 2008/0214988 A1 | 9/2008 | Altshuler et al. |
| 2008/0215038 A1 | 9/2008 | Bakker |
| 2008/0248554 A1 | 10/2008 | Merchant et al. |
| 2008/0262577 A1 | 10/2008 | Altshuler et al. |
| 2008/0294150 A1 | 11/2008 | Altshuler et al. |
| 2008/0294152 A1 | 11/2008 | Altshuler et al. |
| 2008/0294153 A1 | 11/2008 | Altshuler et al. |
| 2008/0306471 A1 | 12/2008 | Altshuler et al. |
| 2008/0319430 A1 | 12/2008 | Zenzie et al. |
| 2009/0018531 A1 | 1/2009 | Welches |
| 2009/0018624 A1 | 1/2009 | Levinson et al. |
| 2009/0024192 A1 | 1/2009 | Mulholland |
| 2009/0024193 A1 | 1/2009 | Altshuler et al. |
| 2009/0043294 A1 | 2/2009 | Island et al. |
| 2009/0048557 A1 | 2/2009 | Yeshurun et al. |
| 2009/0069741 A1 | 3/2009 | Altshuler et al. |
| 2009/0132011 A1 | 5/2009 | Altshuler et al. |
| 2009/0137995 A1 | 5/2009 | Altshuler et al. |
| 2009/0149844 A1 | 6/2009 | Altshuler et al. |
| 2009/0222068 A1 | 9/2009 | Oberreiter et al. |
| 2009/0248004 A1 | 10/2009 | Altshuler et al. |
| 2009/0254076 A1 | 10/2009 | Altshuler et al. |
| 2009/0287195 A1 | 11/2009 | Altshuler et al. |
| 2009/0292277 A1 | 11/2009 | Sierra et al. |
| 2009/0312749 A1 | 12/2009 | Pini et al. |
| 2010/0010507 A1 | 1/2010 | Kinoshita |
| 2010/0015576 A1 | 1/2010 | Altshuler et al. |
| 2010/0021867 A1 | 1/2010 | Altshuler et al. |
| 2010/0036295 A1 | 2/2010 | Altshuler et al. |
| 2010/0049180 A1 | 2/2010 | Wells et al. |
| 2010/0109041 A1 | 5/2010 | Yin et al. |
| 2010/0145321 A1 | 6/2010 | Altshuler et al. |
| 2010/0195680 A1 | 8/2010 | Sierra et al. |
| 2010/0198134 A1 | 8/2010 | Eckhouse et al. |
| 2010/0204686 A1 | 8/2010 | Yaroslavksy et al. |
| 2010/0217248 A1 | 8/2010 | Mirkov et al. |

(56) References Cited

U.S. PATENT DOCUMENTS

| | | |
|---|---|---|
| 2010/0278756 A1 | 11/2010 | Chung et al. |
| 2010/0286673 A1 | 11/2010 | Altshuler et al. |
| 2010/0298744 A1 | 11/2010 | Altshuler et al. |
| 2011/0046523 A1 | 2/2011 | Altshuler et al. |
| 2011/0087155 A1 | 4/2011 | Uhland et al. |
| 2011/0137230 A1 | 6/2011 | Altshuler et al. |
| 2011/0152847 A1 | 6/2011 | Mirkov et al. |
| 2011/0172651 A1 | 7/2011 | Altshuler et al. |
| 2011/0184334 A1 | 7/2011 | Altshuler et al. |
| 2011/0207075 A1 | 8/2011 | Altshuler et al. |
| 2011/0257584 A1 | 10/2011 | Altshuler et al. |
| 2011/0267830 A1 | 11/2011 | Altshuler et al. |
| 2012/0083862 A1 | 4/2012 | Altshuler et al. |
| 2012/0099816 A1 | 4/2012 | Wilson |
| 2012/0116271 A1 | 5/2012 | Caruso et al. |
| 2012/0123399 A1 | 5/2012 | Belikov et al. |
| 2012/0277659 A1 | 11/2012 | Yaroslavsky et al. |
| 2012/0301842 A1 | 11/2012 | Altshuler et al. |

FOREIGN PATENT DOCUMENTS

| | | |
|---|---|---|
| CN | 2053926 | 3/1990 |
| CN | 1073607 | 6/1993 |
| CN | 1182572 A | 5/1998 |
| CN | 1351483 A | 5/2002 |
| CN | 1535126 A | 10/2004 |
| DE | 2826383 | 12/1979 |
| DE | 3304230 A1 | 8/1984 |
| DE | 3719561 A1 | 1/1988 |
| DE | 8807746 | 11/1988 |
| DE | 3837248 | 5/1990 |
| DE | 3841503 | 6/1990 |
| DE | 9102407 | 7/1991 |
| DE | 19803460 | 8/1999 |
| DE | 19944401 A1 | 3/2001 |
| DE | 10112289 | 8/2001 |
| DE | 10140715 A1 | 3/2002 |
| DE | 10120787 | 1/2003 |
| EP | 0142671 | 5/1985 |
| EP | 0172490 A1 | 2/1986 |
| EP | 0297360 | 1/1989 |
| EP | 0320080 A1 | 6/1989 |
| EP | 0324120 A1 | 7/1989 |
| EP | 0413025 | 2/1991 |
| EP | 0458576 | 11/1991 |
| EP | 0563953 | 10/1993 |
| EP | 0565331 | 10/1993 |
| EP | 0575274 | 12/1993 |
| EP | 0593375 | 4/1994 |
| EP | 0598984 | 6/1994 |
| EP | 0709941 | 5/1996 |
| EP | 0724894 | 8/1996 |
| EP | 0726083 | 8/1996 |
| EP | 0736308 | 10/1996 |
| EP | 0743029 | 11/1996 |
| EP | 0743029 A2 | 11/1996 |
| EP | 0755698 | 1/1997 |
| EP | 0763371 | 3/1997 |
| EP | 0765673 | 4/1997 |
| EP | 0765674 | 4/1997 |
| EP | 0783904 | 7/1997 |
| EP | 0884066 | 12/1998 |
| EP | 0885629 | 12/1998 |
| EP | 0920840 A2 | 6/1999 |
| EP | 0927544 | 7/1999 |
| EP | 1038505 | 9/2000 |
| EP | 1057455 | 12/2000 |
| EP | 1075854 | 2/2001 |
| EP | 1138269 | 10/2001 |
| EP | 1138349 | 10/2001 |
| EP | 1147785 | 10/2001 |
| EP | 1219258 | 7/2002 |
| EP | 1226787 | 7/2002 |
| EP | 1238683 A1 | 9/2002 |
| EP | 1250893 | 10/2002 |
| EP | 1250893 A2 | 10/2002 |
| EP | 1057454 | 11/2003 |
| EP | 1 457 234 A2 | 9/2004 |
| EP | 1495735 A1 | 1/2005 |
| EP | 1512373 A1 | 3/2005 |
| EP | 1535582 A1 | 6/2005 |
| EP | 1 627 662 | 2/2006 |
| EP | 1650615 | 4/2006 |
| EP | 1797836 | 6/2007 |
| EP | 1839705 A1 | 10/2007 |
| EP | 1854505 A2 | 11/2007 |
| FR | 2199453 | 4/1974 |
| FR | 2591902 | 6/1987 |
| GB | 1251424 | 10/1971 |
| GB | 1546625 | 5/1979 |
| GB | 2044908 | 10/1980 |
| GB | 2059053 A | 4/1981 |
| GB | 2059054 A | 4/1981 |
| GB | 2123287 | 2/1984 |
| GB | 2212010 | 7/1989 |
| GB | 2239675 A | 7/1991 |
| GB | 2270159 A | 3/1994 |
| GB | 2356570 | 5/2001 |
| GB | 2360461 A | 9/2001 |
| GB | 2360946 | 10/2001 |
| GB | 2364376 A | 1/2002 |
| GB | 2368020 | 4/2002 |
| GB | 2390021 | 12/2003 |
| GB | 2397528 | 7/2004 |
| JP | 5412979 | 10/1979 |
| JP | S5552766 A | 4/1980 |
| JP | S55771871 A | 6/1980 |
| JP | S574007 A | 1/1982 |
| JP | S62165985 A | 7/1987 |
| JP | S6323648 A | 1/1988 |
| JP | S63249577 A | 10/1988 |
| JP | 64-027554 A | 1/1989 |
| JP | S6481222 A | 3/1989 |
| JP | 1099574 A | 4/1989 |
| JP | H022199 A | 1/1990 |
| JP | 2174804 | 7/1990 |
| JP | H02285694 A | 11/1990 |
| JP | H0319385 A | 1/1991 |
| JP | H0316956 U | 2/1991 |
| JP | 3066387 A | 3/1991 |
| JP | H03183184 A | 8/1991 |
| JP | 199013014 A | 9/1991 |
| JP | 6022871 | 2/1994 |
| JP | H06154239 A | 6/1994 |
| JP | H079179 A | 1/1995 |
| JP | 7063957 A | 3/1995 |
| JP | H07328025 A | 12/1995 |
| JP | H0815539 A | 1/1996 |
| JP | H0854538 A | 2/1996 |
| JP | 9084803 A | 3/1997 |
| JP | H09141869 | 6/1997 |
| JP | 10014661 | 1/1998 |
| JP | 10-503109 A | 3/1998 |
| JP | 10165410 A | 6/1998 |
| JP | 11047146 A | 2/1999 |
| JP | 11081877 A | 3/1999 |
| JP | 2000037400 A | 2/2000 |
| JP | 2000-153003 A | 6/2000 |
| JP | 2000300684 A | 10/2000 |
| JP | 2001000560 A | 1/2001 |
| JP | 2001029124 A | 2/2001 |
| JP | 2001145520 | 5/2001 |
| JP | 2001196665 A | 7/2001 |
| JP | 2001343560 A | 12/2001 |
| JP | 2002506362 T | 2/2002 |
| JP | 2002272861 | 9/2002 |
| JP | 2003052843 A | 2/2003 |
| JP | 2005017796 A | 1/2005 |
| JP | 2003192809 | 2/2005 |
| JP | 2006192073 A | 7/2006 |
| RU | 2082337/95105406 | 6/1997 |
| RU | 2089126/94012665 | 10/1997 |
| RU | 2089127/94040344 | 10/1997 |

(56) References Cited

FOREIGN PATENT DOCUMENTS

| | | |
|---|---|---|
| RU | 2096051/95012749 | 11/1997 |
| RU | 2122848/4954402 | 10/1998 |
| WO | WO 86/02783 | 5/1986 |
| WO | WO 88/04592 | 6/1988 |
| WO | WO 90/00420 | 1/1990 |
| WO | WO 9006727 | 6/1990 |
| WO | WO 9012548 | 11/1990 |
| WO | WO 9101053 | 1/1991 |
| WO | 9102562 A1 | 3/1991 |
| WO | WO 9112050 | 8/1991 |
| WO | WO 91/13652 | 9/1991 |
| WO | WO 9113653 | 9/1991 |
| WO | WO 9118646 | 12/1991 |
| WO | WO 92/16338 | 1/1992 |
| WO | WO 9203977 | 3/1992 |
| WO | WO 9206739 | 4/1992 |
| WO | WO 92/19165 | 11/1992 |
| WO | WO 93/05920 | 4/1993 |
| WO | WO 9321843 | 11/1993 |
| WO | WO 9503089 | 2/1995 |
| WO | WO 9504393 | 2/1995 |
| WO | 9510243 | 4/1995 |
| WO | WO 9514251 | 5/1995 |
| WO | WO 95/15725 | 6/1995 |
| WO | WO 95/32441 | 11/1995 |
| WO | WO 9533518 | 12/1995 |
| WO | WO 9609853 | 4/1996 |
| WO | WO 9618347 | 6/1996 |
| WO | 96/24406 A1 | 8/1996 |
| WO | WO-96/22741 A1 | 8/1996 |
| WO | WO 96/23447 | 8/1996 |
| WO | WO 96/25979 | 8/1996 |
| WO | WO 9622813 | 8/1996 |
| WO | WO 9624182 | 8/1996 |
| WO | 9628212 A1 | 9/1996 |
| WO | WO 96/36396 | 11/1996 |
| WO | WO 96/41579 | 12/1996 |
| WO | WO 9639734 | 12/1996 |
| WO | WO 97/13458 | 4/1997 |
| WO | WO 97/13552 | 4/1997 |
| WO | 9722384 A1 | 6/1997 |
| WO | 9728752 A1 | 8/1997 |
| WO | WO 9737602 | 10/1997 |
| WO | WO 9737723 | 10/1997 |
| WO | 9805286 A1 | 2/1998 |
| WO | 9806456 | 2/1998 |
| WO | WO 98/04317 | 2/1998 |
| WO | WO 98/05380 | 2/1998 |
| WO | WO-98/07379 A1 | 2/1998 |
| WO | WO-98/20937 A2 | 5/1998 |
| WO | WO 98/24507 | 6/1998 |
| WO | 98/29134 A2 | 7/1998 |
| WO | WO-98/41158 A1 | 9/1998 |
| WO | WO 98/51235 | 11/1998 |
| WO | WO 98/52481 | 11/1998 |
| WO | WO 98/58595 | 12/1998 |
| WO | 9910046 | 3/1999 |
| WO | WO 99/17666 | 4/1999 |
| WO | WO 99/17667 | 4/1999 |
| WO | WO-9917668 A1 | 4/1999 |
| WO | WO 99/27997 | 6/1999 |
| WO | WO 99/29243 | 6/1999 |
| WO | 9934867 A1 | 7/1999 |
| WO | WO 99/38569 | 8/1999 |
| WO | WO 9939410 | 8/1999 |
| WO | 9943387 | 9/1999 |
| WO | 9944638 A1 | 9/1999 |
| WO | WO 99/46005 | 9/1999 |
| WO | WO 99/49937 | 10/1999 |
| WO | WO 9958195 | 11/1999 |
| WO | 9962472 | 12/1999 |
| WO | 9966988 A1 | 12/1999 |
| WO | WO 00/02491 | 1/2000 |
| WO | WO 00/03257 | 1/2000 |
| WO | 0007514 A1 | 2/2000 |
| WO | 0030714 A1 | 6/2000 |
| WO | WO 00/32272 | 6/2000 |
| WO | 0041278 A1 | 7/2000 |
| WO | WO 00/40266 | 7/2000 |
| WO | WO 00/43070 | 7/2000 |
| WO | 0044294 A1 | 8/2000 |
| WO | WO 00/44294 | 8/2000 |
| WO | 0054685 A2 | 9/2000 |
| WO | WO 00/54649 | 9/2000 |
| WO | WO 0053113 | 9/2000 |
| WO | 0062700 A1 | 10/2000 |
| WO | WO 00/64537 | 11/2000 |
| WO | WO 00/71045 | 11/2000 |
| WO | WO-0066226 A1 | 11/2000 |
| WO | WO 00/74583 | 12/2000 |
| WO | WO 00/74781 | 12/2000 |
| WO | WO 00/78242 | 12/2000 |
| WO | WO 01/03257 | 1/2001 |
| WO | 0114012 A1 | 3/2001 |
| WO | WO 01/26573 | 4/2001 |
| WO | WO 01/34048 | 5/2001 |
| WO | 01/41872 A1 | 6/2001 |
| WO | WO 01/42671 | 6/2001 |
| WO | WO 01/54606 | 8/2001 |
| WO | WO 01/54770 | 8/2001 |
| WO | 0178830 A2 | 10/2001 |
| WO | WO 01/78830 | 10/2001 |
| WO | 0209813 A1 | 2/2002 |
| WO | 0226147 A1 | 4/2002 |
| WO | WO 02/053050 | 7/2002 |
| WO | WO 02053050 | 7/2002 |
| WO | WO 02/069825 | 9/2002 |
| WO | 02078559 A1 | 10/2002 |
| WO | WO 02/094116 | 11/2002 |
| WO | 03005883 A2 | 1/2003 |
| WO | 03049633 A1 | 6/2003 |
| WO | 04000150 A1 | 12/2003 |
| WO | WO 03103529 | 12/2003 |
| WO | WO-2004/011848 A2 | 2/2004 |
| WO | WO 2004/033040 | 4/2004 |
| WO | 2004037068 A2 | 5/2004 |
| WO | 2004037287 A2 | 5/2004 |
| WO | 2004080279 A2 | 9/2004 |
| WO | WO 2004/073537 | 9/2004 |
| WO | 2004/086947 A2 | 10/2004 |
| WO | WO 2004/084752 | 10/2004 |
| WO | WO 2004/086947 A2 | 10/2004 |
| WO | WO 2005/007003 A1 | 1/2005 |
| WO | WO 2005/009266 | 2/2005 |
| WO | WO 2005/030317 | 4/2005 |
| WO | WO-2005/046793 A2 | 5/2005 |
| WO | 2005065288 A2 | 7/2005 |
| WO | 2005092438 A1 | 10/2005 |
| WO | 2005096981 A2 | 10/2005 |
| WO | 2005099369 A2 | 10/2005 |
| WO | WO 2005/112815 | 12/2005 |
| WO | 2006006123 A1 | 1/2006 |
| WO | WO 2006/036968 A2 | 4/2006 |
| WO | WO-2006066226 A1 | 6/2006 |
| WO | 2006089227 A2 | 8/2006 |
| WO | 2006101735 A1 | 9/2006 |
| WO | 2006116141 A1 | 11/2006 |
| WO | 2007035444 A2 | 3/2007 |
| WO | WO-2007122611 A2 | 11/2007 |
| WO | WO 2008007218 | 1/2008 |
| WO | 2008070747 A2 | 6/2008 |
| WO | WO 2008153999 | 12/2008 |
| WO | WO 2010102255 | 9/2010 |

OTHER PUBLICATIONS

Chan, E.K., "Effects of Compression on Soft Tissue Optical Properties," IEEE Journal of Selected Topics in Quantum Electronics, vol. 2, No. 4, pp. 943-950 (Dec. 1996).

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987).

(56) References Cited

OTHER PUBLICATIONS

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987).
Apfelberg et al. "Analysis of Complications of Argon Laser Treatment for Port Wine Hemangiomas with Reference to Striped Technique," Lasers in Surgery and Medicine, 2:357-371 (1983).
Dixon et al. "Hypertrophic Scarring in Argon Laser Treatment of Port-Wine Stains," Plastic and Reconstructive Surgery, 73:771-777 (1984).
Ginsbach et al. "New Aspects in the Management of Benign Cutameous Tumors," Laser 79 Opto-Electronics, Munich Conference Proceedings, 344-347 (1979).
Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981).
Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984).
Hulsbergen Henning et al., "Port Wine Stain Coagulation Experiments with a 540-nm Continuous Wave Dye-Laser," Lasers in Surgery and Medicine, 2:205-210 (1983).
Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996).
Rubach et al., "Histological and Clinical Evaluation of Facial Resurfacing Using a Carbon Dioxide Laser With the Computer Pattern Generator," Arch Otolaryngol Head Neck Surg., 123:929-934 (1997).
Unger, "Laser Hair Transplantation III, Computer-assisted Laser Transplanting," Dermatol. Surg., 21:1047-1055 (1995).
Sheehan-Dare, et al., "Lasers in Dermatology," British Journal of Dermatology, 129:1-8 (1993).
Rotteleur, et al., "Robotized scanning laser handpiece for the treatment of port wine stains and other angiodysplasias," Lasers Surg. Med., 8:283-287 (1998).
Nemeth, et al., "Copper vapor laser treatment of pigmented lesions," Lasers Surg. Med. Supp. 2:51 (1990).
McDaniel, et al., "Hexascan: A New Robotized Scanning Laser Handpiece," Cutis, 45:300-305 (1990).
Levin, G. et al., "Designing with hyseretic current-mode control, " EDN Magazine, pp. 1-8, Apr. 28, 1994.
Levin, G. et al., "Designing with hyseretic current-mode control, " EDN Magazine, pp. 1-8, Apr. 11, 1996.
Gottlieb, I., "Power Supplies, Switching Regulators, Inverters & Converters," 1976.
Shumilovitch et al., "Influence of Low Intensity Laser Radiation Upon the Microflora of Carious Cavities and Root Canal," SPIE vol. 1984, pp. 215-220.
Sandford et al., "Thermal Effects During Desensitisation of Teeth with Gallium—Aluminum—Arsenide Lasers," University of Queensland Dental School, Periodontology 15: 25-30 (1994).
Forrest-Winchester et al., "The Effect of Infrared Laser Radiation on Dentinal Permeability in vitro," Department of Dentistry, University of Queensland Dental School, pp. 1-8, 1992.
Powell, "Laser Dental Decay Prevention: does it have a future?" SPIE vol. 3192, 1997.
Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998.
Blankenau et al., "In Vivo Caries-Like Lesion Prevention with Argon Laser: Pilot Study," Journal of Clinical Laser Medicine and Surgery, vol. 17, No. 6, pp. 241-243, 1999.
Hsu et al., "Combined Effects of Laser Irradiation/Solution Flouride Ion on Enamel Demineralization," Journal of Clinical Laser Medicine and Surgery, vol. 16, No. 2 pp. 93-105, 1998.
Hicks et al., "After Low Fluence Argon Laser and Flouride Treatment," Compendium, vol. 18, No. 6, Jun. 1997.
Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995.
Oleinik, et al., "Automatized Securing Definition for Laser Therapy Indications in Case of Non-complicated Caries," SPIE, vol. 1984, pp. 238-244.
Kazmina et al., "Laser Prophlaxis and Treatment of Primary caries," SPIE vol. 1984, pp. 231-233.
Sokolova et al., "Low-intense Laser Radiation in Complex Treatment of Inflammatory Diseases of Parodontium," SPIE vol. 1984, pp. 234-237.
Petrischev et al. "Clinical and Experimental Low-Intense Laser Therapy in Dentistry," SPIE, vol. 1984, pp. 212-214.
Mamedova et al., "Microbiological Estimate of Parodontis Laser Therapy Efficiency," SPIE vol. 1984, pp. 247-249.
Kozlov et al., "Laser in Diagnostics and Treatment of Microcirculation Disorders Under Parodontitis," SPIE vol. 1984, pp. 253-264.
Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230.
Walsh, "Laser "Curettage": a Critical Analysis," Periodontology 14:4-12, 1993.
Ozawa et al., "Stimulatory Effects of Low-Power Laser Irradiation on Bone Formation in vitro," SPIE vol. 1984, pp. 281-288.
Shimizu et al., "Prospect of Relieving Pain Due to Tooth Movement During Orthodontic Treatment Utilizing a GA-AI as Diode Laser," SPIE vol. 1984, pp. 275-280.
Petrischev et al., "Report on Low Intensity Laser Radiation Usage in Dentistry," SPIE vol. 1984, pp. 202-211.
Karu, "Photobiological Fundamentals of Low-Power Laser Therapy," 8th Congress of International Society for Laser Surgery and Medicine, Mar. 30, 1987.
Schindl, "Does Low Intensity Laser Irradiation Really Cause Cell Damage?" Laser in Surgery and Medicine vol. 22, pp. 105, 2001.
Grossman, et al., "780 nm Low Power Diode Laser Irradiation Stimulates Proliferation of Keratinocyte Cultures: Involvement of Reactive Oxygen Species," Lasers in Surgery and Medicine vol. 29, pp. 212-218, 1998.
Karu, "Cell Attachment to Extracellular Matrics is Modulated by Pulsed Radiation at 820 nm and Chemicals that Modify the Activity of Enzymes in the Plasma Membrane," Laser in Surgery and Medicine, vol. 29, pp. 274-281, 2001.
Maegawa, et al., "Effects of Near-Infrared Low-Level Laser Irradiation on Microcirculation," Lasers in Surgery and Medicine, vol. 27, pp. 427-437, 2000.
Van Bruegel, "Power Density and Exposure Time of He—Ne Irradiation Are More Important Than Total Energy Dose in Photo-Biomodulation of Human Fibroblasts in Vitro," Lasers in Surgery and Medicine, vol. 12 pp. 528-537, 1992.
European Summons to Attend Oral Proceedings issued Aug. 13, 2012 for Application No. 03737199.4 (4 Pages).
European Search Report, European Patent Application No. 10012969.1, Dated Jul. 13, 2011.
[No Author] Webpage www.gallery.com—Rutile (Titanium Oxide)—Retrieved Oct. 3, 2011 from Http://www.galleries.com/minerals/oxides/rutile/rutile.htm. 2 pages.
IPG Data Sheet for TFL Thulium Laser, Jun. 2001.
Altea Therapeutics—Medicines Made Better (single page website print-out), Sep. 30, 2004.
G.B. Altshuler et al., "Acoustic response of hard dental tissues to pulsed laser action," SPIE, vol. 2080, Dental Application of Lasers, pp. 97-103, 1993.
G.B. Altshuler et al., "Extended theory of selective photothermolysis," Lasers in Surgery and Medicine, vol. 29, pp. 416-432, 2001.
R.L. Amy & R. Storb, "Selective mitochondrial damage by a ruby laser microbeam: An electron microscopic study," Science, vol. 15, pp. 756-758, Nov. 1965.
R.R. Anderson et al., "The optics of human skin," Journal of Investigative Dermatology, vol. 77, No. 1, pp. 13-19, 1981.

(56) References Cited

OTHER PUBLICATIONS

R.R. Anderson & J.A. Parrish, "Selective photothermolysis: Precise microsurgery by selective absorption of pulsed radiation," Science, vol. 220, pp. 524-527, Apr. 1983.
A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.
P. Bjerring et al., "Selective Non-Ablative Wrinkle Reduction by Laser," J Cutan Laser Ther, vol. 2, pp. 9-15, 2000.
Derma Chiller advertisement (2 pages) from Paradigm Trex.
Doukas et al., "Transdermal Drug Delivery With a Pressure Wave," Advanced Drug Delivery Reviews 56 (2004), pp. 559-579.
J.S. Dover et al., "Pigmented guinea pig skin irradiated with Q-switched ruby laser pulses," Arch Dermatol, vol. 125, pp. 43-49, Jan. 1989.
L.H. Finkelstein & L.M. Blatstein, "Epilation of hair-bearing urethral grafts using the neodymium:yag surgical laser," Journal of Urology, vol. 146, pp. 840-842, Sep. 1991.
E.J. Fiskerstrand et al., "Hair Removal With Long Pulsed Diode Lasers: A Comparison Between Two Systems With Different Pulse Structures," Lasers in Surgery and Medicine, vol. 32, pp. 399-404, 2003.
L. Goldman, Biomedical Aspects of the Laser, Springer-Verlag New York Inc., publishers, Chapts. 1, 2, & 23, 1967.
L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.
L. Goldman, "Effects of new laser systems on the skin," Arch Dermatol., vol. 108, pp. 385-390, Sep. 1973.
L. Goldman, "Laser surgery for skin cancer," New York State Journal of Medicine, pp. 1897-1900, Oct. 1977.
L. Goldman, "Surgery by laser for malignant melanoma," J. Dermatol. Surg. Oncol., vol. 5, No. 2, pp. 141-144, Feb. 1979.
L. Goldman, "The skin," Arch Environ Health, vol. 18, pp. 434-436, Mar. 1969.
L. Goldman & D.F. Richfield, "The effect of repeated exposures to laser beams," Acta derm.-vernereol., vol. 44, pp. 264-268, 1964.
L. Goldman & R.J. Rockwell, "Laser action at the cellular level," JAMA, vol. 198, No. 6, pp. 641-644, Nov. 1966.
L. Goldman & R.G. Wilson, "Treatment of basal cell epithelioma by laser radiation," JAMA, vol. 189, No. 10, pp. 773-775.
L. Goldman et al., The biomedical aspects of lasers, JAMA, vol. 188, No. 3, pp. 302-306, Apr. 1964.
L. Goldman et al., "Effect of the laser beam on the skin, Preliminary report" Journal of Investigative Dermatology, vol. 40, pp. 121-122, 1963.
L. Goldman et al., "Effect of the laser beam on the skin, III. Exposure of cytological preparations," Journal of Investigative Dermatology, vol. 42, pp. 247-251, 1964.
L. Goldman et al., "Impact of the laser on nevi and melanomas," Archives of Dermatology, vol. 90, pp. 71-75, Jul. 1964.
L. Goldman et al., "Laser treatment of tattoos, A preliminary survey of three year's clinical experience," JAMA, vol. 201, No. 11, pp. 841-844, Sep. 1967.
L. Goldman et al., "Long-term laser exposure of a senile freckle," ArchEnviron Health, vol. 22, pp. 401-403, Mar. 1971.
L. Goldman et al., "Pathology, Pathology of the effect of the laser beam on the skin," Nature, vol. 197, No. 4870, pp. 912-914, Mar. 1963.
L. Goldman et al., "Preliminary investigation of fat embolization from pulsed ruby laser impacts of bone," Nature, vol. 221, pp. 361-363, Jan. 1969.
L. Goldman et al., "Radiation from a Q-switched ruby laser, Effect of repeated impacts of power output of 10 megawatts on a tattoo of man," Journal of Investigative Dermatology, vol. 44, pp. 69-71, 1965.
L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.
M.C. Grossman et al., "Laser Targeted at Hair Follicles," Lasers Med Surg., Suppl. 7:221,1995.
E. Klein et al., "Biological effects of laser radiation 1.,"Northeast Electroncis Research and Engineering Meeting, NEREM Record, IEEE catalogue No. F-60, pp. 108-109, 1965.
J.G. Kuhns et al., "Laser injury in skin," Laboratory Investigation, vol. 17, No. 1, pp. 1-13, Jul. 1967.
J.G. Kuhns et al., "Biological effects of laser radiation II Effects of laser irradiation on the skin," NEREM Record, pp. 152-153, 1965.
D. Manstein et al., "Selective Photothermolysis of Lipid-Rich Tissue," American Society for Laser Medicine and Surgery Abstracts, No. 17, American Society for Laser Medicine and Surgery Twenty-First Annual Meeting, Apr. 20-22, 2001, p. 6.
R.J. Margolis et al., "Visible action spectrum for melanin-specific selective photothermolysis," Lasers in Surgery and Medicine, vol. 9, pp. 389-397, 1989.
Ohshiro et al., "The Ruby and Argon Lasers in the Treatment of the Naevi," Annals Academy of Medicine, Apr. 1983, vol. 12, No. 2, pp. 388-395.
J.A. Parrish, "Selective thermal effects with pulsed irradiation from lasers: From organ to organelle," Journal of Investigative Dermatology, vol. 80, No. 6 Supplement, pp. 75s-80s, 1983.
L. Polla et al., "Melanosomes are a primary target of Q-switched ruby laser irradiation in guinea pig skin," Journal of Investigative Dermatology, vol. 89, No. 3, pp. 281-286, Sep. 1987.
Riggle et al., "Laser Effects on Normal and Tumor Tissue," Laser Applications in Medicine and Biology, vol. 1, M.L. Wolbarsht, editor, Plenum Press, publishers, Chapter 3, pp. 35-65, 1971.
T. Shimbashi & T. Kojima, "Ruby laser treatment of pigmented skin lesions," Aesth. Plast. Surg., vol. 19, pp. 225-229, 1995.
Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.
Sumian, C.C. et al., "A Preliminary Clinical and Histopathological Study of Laser Skin Resurfacing Using a Frequency-Doubled Nd:YAG Laser After Application of Chromofilm®," Journal of Cutaneous Laser Therapy, vol. 1, pp. 159-166, 1999.
Sumian, C.C. et al., "Laser Skin Resurfacing Using a Frequency Doubled Nd:YAG Laser After Topical Application of an Exogenous Chromophore," Lasers in Surgery and Medicine, vol. 25, pp. 43-50, 1999.
C.R. Taylor et al., "Treatment of tattoos by Q-switched ruby laser," Arch. Dermatol. vol. 126, pp. 893-899, Jul. 1990.
V.V. Tuchin, "Laser light scattering in biomedical diagnostics and therapy," Journal of Laser Applications, vol. 5, No. 2-3, pp. 43-60, 1993.
S. Watanabe et al, "Comparative studies of femtosecond to microsecond laser pulses on selective pigmented cell injury in skin," Photochemistry and Photobiology, vol. 53, No. 6, pp. 757-762, 1991.
A.J. Welch et al., "Evaluation of cooling techniques for the protection of the epidermis during HD-yag laser irradiation of the skin," Neodymium-Yag Laser in Medicine and Surgery, Elsevier Science Publishing Co., publisher, pp. 195-204, 1983.
R.B. Yules et al., "The effect of Q-switched ruby laser radiation on dermal tattoo pigment in man," Arch Surg, vol. 95, pp. 179-180, Aug. 1967.
E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.
Abstracts Nos. 17-19, Lasers in Surgery and Medicine, ASLMS, American Society for Laser Medicine and Surgery, Apr. 20, 2001.
Abstracts Nos. 219-223, ASLMS, American Society for Laser Medicine and Surgery, Apr. 20, 2001.
Invention description to certificate of authorship, No. 532304, "The way of investigation of radiation time structure of optical quantum generator", Sep. 7, 1974.
Invention description to certificate of authorship, No. 719439, "The ring resonator of optical quantum generator", Aug. 15, 1975.

(56) References Cited

OTHER PUBLICATIONS

Invention description to certificate of authorship, No. 741747, "The modulator of optical radiation intensity", Oct. 10, 1977.
Invention description to certificate of authorship, No. SU 1257475 A1, "Laser interferometric device to determine no-linearity of an index of refraction of optical medium", Sep. 4, 1985.
Invention description to certificate of authorship, No. SU 1326962 A1, "The way of determination of non-linearity of an index of refraction of optical medium", Mar. 31, 1986.
Altshuler et al., "Modern Optics and Dentistry," Laser in Dentistry, pp. 283-297, 1995.
Altshuler et al., "New Optical Effects in the Human Hard Tooth Tissues," Lasers and Medicine, Proc. SPIE vol. 1353, pp. 97-102, 1989.
Altshuler et al., "Human Tooth as an Optical Device," SPIE vol. 1429 Holography and Interferometry and Optical Pattern Recognition in Biomedicine, pp. 95-104, 1991.
Ohbayashi, "Stimulatory Effect of Laser Irradiation on Calcified Nodule Formation in Human Dental Pulp Fibroblasts," Abstract J-Endod. Jan. 1999; 25(1): 30-3.
Orchardson, "Effect of Pulsed Nd:YAG Laser Radiation on Action Potential Conduction in Nerve Fibres Inside Teeth in vitro," Abstract J-Dent. Jul.-Aug. 1998; 26(5-6): 421-6.
Dabrowska, "Intravital Treatment of the Pulp with Stimulation Laser Biostimulation," Abstract Rocz-Akad-Med-Bialymst. 1997; 42(1): 168-76.
Sing, "Electroacupuncture and Laser Stimulation Treatment: Evaluation by Somatosensory Evoked Potential in Conscious Rabbits," Abstract Am-J-Chin-Med. 1997; 25(3-4): 263-71.
Walsh, "The Current Status of Low Level Laser Therapy in Dentistry. Part 1. Soft Tissue Applications" paper prepared by LJ Walsh, Department of Dentistry University of Queensland, pp. 1-16. Publication date unknown.
Zonios et al., "Skin Melanin, Hemoglobin, and Light Scattering Properties can be Quantitatively Assessed in Vivo Using Diffuse Reflectance Spectroscopy," Journal of Investigative Dermatology, V. 117: 1452-1457 (Dec. 2001).
Remillard et al., "Diode laser illuminated automotive brake lamp using a linear fanout diffractive optical element," Proc. of the Diffractive Optics and Micro-Optics Conference, OSA Technical Digest Series vol. 10, 192-194 (1998).
Remillard et al., "Diode Laser Illuminators for Night-Vision Applications," SPIE Proceedings vol. 4285:14-22 (2001).
Marinelli et al., "Diode laser illuminated automotive lamp systems," SPIE Proceedings vol. 3285:170-177 (1998).
Rohrer, "Evaluating the Safety and Efficacy of a Novel Light Based Hair Removal System," Lasers. Surg. Med. Supp.13:97 (2001).
Sliney et al., "Safety with Lasers and Other Optical Sources: A Comprehensive Handbook," Plenum Press, pp. 477-480 (1980).
Watanabe, S. et al., "The Effect of Pulse Duration on Selective Pigmented Cell Injury by Dye Lasers," The Journal of Investigative Dermatology, 88:523, 1987.
"Bioptron Light Therapy System," website print-out, accessed Jul. 13, 2006 (2 pages).
[No Author] Energy Systems Cororpation, "A Practical Guide for the PhotoDern.RTM.VL user," Haifa, Israel, Commercial Brochure 8 Pages, Oct. 1995.
[No Author] "Final Report on the LFDL-10 Laser System for the GCA Corporation," Candela Corp., Natick, MA, Section II, subsection 5, pp. 13-15 & 27, Mar. 1982.
[No Author] "Fractional Photothermolysis Redefines Facial Skin Regeneration Science," Aesthetic Buyers Guide, Mar./Apr. 2004, www.miinews.com, pp. 1-4.
[No Author] "Hydrogel Dressings Contain Particles During Laser Therapy," Dermatology Times, ISSN-01966197, p. 26 (1994).
[No Author] "Instruction Manual, TFDL-10," Adapted for SLAC, Candela Corporation, Natick, Oct. 1985.
[No Author] "Lasers Battle for Prostatectomy Market," Medical Laser Industry Report, 5:1-3 (Aug. 1991).
[No Author] "LFDL-8 Instruction Manual," Candela Laser Corporation, Wayland, MA Revised Oct. 1987.
[No Author] "LFDL-8 Instruction Manual," Candela Laser Corporation, Wayland, MA, Jan. 1982, Revised Jun. 1987.
[No Author] "LFDL-8 Instruction Manual," Cynosure, Inc., Bedford, MA, Revised Nov. 1992.
[No Author] "Prostate Enlargement: Benigh Prostatic Hyperplasia," brochure from U.S. Department of Health and Human Services, pp. 1-14, (at least by 1992).
[No Author] "Special Instruction and Test Results for the LFDL-2 Wave Guide Laser," Candela Laser Corporation, Wayland, MA, Sep. 1982.
[No Author] "The Laser TURP Advantage," INTRA-SONIX, Inc. pp. 1-4 (1991).
[No Author] Beckman Laser Institute "Experimental PDT to Prevent Esophegus Cancer," (8 pages) 1996.
[No Author] Cynosure Dioderm 510(k) Notification K992765 for Cynosure, Inc. to Food and Drug Administration, dated: Aug. 16, 1999 and Aug. 20, 1999 (Additional Information).
[No Author] Reliant Technologies, Inc. "Physicians Guide: Understanding Fraxel Laser Treatment," pp. 1-10 (2004).
[No Author] Ritter Sybron Corporation, "Electrosurgery, A Guide for Operating Room Personnel," pp. 1-22, (Jun. 1976).
[No Author] Selective Photothermolysis of Sebaceous Glands, Department of Health and Human Services, Public Health Service, Small Business Innovation Research Program II Grant Application, Cynosure, Inc., dated: Jul. 27, 2000, pp. 17-39 and 43-44.
"American Society for Laser Medicine and Surgery Abstracts," Lasers in Surgery and Medicine, Supplement 6, p. 46 (1994).
Anderson, R.R., et al., "Microvasculature Can Be Selectively Damaged Using Dye Lasers: A Basic Theory and Experimental Evidence in Human Skin," Lasers in Surgery and Medicine 1:263-276 (1981).
Altshuler, et al., "Self Canalization of Laser Microbeam in Tissue as Fundamental Mechanism of Fractional Skin Resurfacing", Lasers in Surgery and Medicine Supple 15, 21, 2003.
Angelis, et al., "Fractional, Non-Ablative Laser Therapy for the Treatment of Striae Distensae", White Paper published by Palomar Medical Technologies, Inc. (2009)5 pages.
Apfelberg, D.B., "A Preliminary Study of the Combined Effect of Neodymium:YAG Laser Photocoagulation and Direct Steroid Instillation in the Treatment of Capillary/Cavernous Hemangiomas of Infancy," Department of Plastic Surgery and Comprehensive Laser Center, Palo Alto Medical Foundation, Palo Alto, CA, pp. 94-103 (1989).
Apfelberg, D.B., "Combination Treatment for Massive Cavernous Hemangioma of the Face: YAG Laser Photocoagulation Pulse Direct Steroid Injection Followed by YAG Laser Resection with Sapphire Scalpel Tips, Aided by Superselective Embolization," Lasers in Surgery and Medicine, 10:217-223 (1990).
Benjavitvilai, C. et al., "Fuzzy Calibration of Magnetometer in Presence of Surgical Microscope," 2005 27th Annual International Conference of the IEEE Engineering in Medicine and Biology Society (IEEE Cat. No. 05CH37611C), Shanghai, China, Aug. 31-Sep. 3, 2005.
Bogdan Allemann, et al., "Laser Principles", Physical and Electronic Properties of Lasers, Basics in Dermatological Laser Applications, Curr. Probl. Dermatol, Basel, Karger. Zurich, Switzerland and Miami, Florida. vol. 42, pp. 7-23, 2011, 17 pages.
Bohm et al., "The Pilosebaceous Unit is Part of the Skin Immune System," Dermatology, 196:75-79, 1998.
Boiteux, M., et al., "A Transverse Flow Repetitive Dye Laser," Applied Optics, 9, 514 (1970).
Boulnois, J., "Photophysical Processes in Recent Medical Laser Developments: a Review," Lasers in Medical Science, vol. 1:47-66 (1986).
Britt et al., "The Effect of pH or Photobleaching of Organic Laser Dyes", IEEE J. Quantum Electron. (Dec. 1972), 913-914.
Burlamacchi et al, "A Simple Reliable Waveguide Dye Laser for Ophthalmological Applications," Rev of Sci Instrum; vol. 46; No. 3; pp. 281-283, Mar. 1975.
Costello, A. et al., "Nd:YAG Laser Ablation of the Prostate as a Treatment for Benign Prostatic Hypertrophy," Lasers in Surgery and Medicine, 12:121-124 (1992).

(56) References Cited

OTHER PUBLICATIONS

Cunliffe, "Acne Vulgaris. The Past, the Present and the Future," Acta Bermatovener (Stockh) Suppl. 120, pp. 34-38, 1985.
Dierickx, C.C. et al., "Thermal Relaxation of Port-wine Stain Vessels Probed In Vivo: The Need for 1-10 Millisecond Laser Pulse Treatment," The Journal for Investigative Dermatology, pp. 709-714 (1995).
Dock et al., "Clinical Histologic and Ultrastructural Evaluation of Solar Elastosis Treated With the Pulsed Dye Laser," American Society for Laser Medicine and Surgery Abstracts, p. 54 (Apr. 1997).
Dufresne et al., "Squamous cell carcinoma arising from the follicular occlusion triad," J. Am. Acad. Dermatol. 35(3), Part 1:475-477, 1996.
Fallon Friedlander, "Effective Treatment of Acne Fulminans-Associated Granulation Tissue with the Pulsed Dye Laser," Pediatric Dermatology, 15(5):396-398, 1998.
Ellenberger, et al. "Single-Frequency Nd:Glass Laser Oscillator with Pulse-Transmission-Mode Q-Switch with Pulse-Transmission-Mode Q-Switch," Optics communication, vol. 81, No. 6 (Mar. 1991).
Fletcher, A.N. et al., "Improving the Output and Lifetime of Flashlamp-Pumped Dye Lasers" Proceedings of the International Conference on Lasers '85, pp. 797-804, Dec. 2-6, 1985.
Friedman-Binrbaum et al., "Seborrheic Skin and Acne Vulgaris as Protective Factors against the Development of Basal Cell Epithelioma," Dermatolgica, 183:160-163, 1991.
Furomoto, H., "Dye Chemisry and System Study for Optimum Laser Operation at 436 NM Using the LFDL-10 Laser," Prepared for Burlington Division Geophysical Corporation of America, pp. 1-23, Mar. 1982.
Goldberg, "Lasers for Facial Rejuvenation", Am J. Clin. Dermatol., 4(4):225-234, 2003, 10 pages.
Goldberg, "Nonablative Resurfacing", Clinics in Plastic Surgery, Skin Laser and Surgery Specialists of New York and New Jersey. Westwood, New Jersey. vol. 27, No. 2, Apr. 2000, 6 pages.
Goldman, M. P., "Leg Veins and Lasers," American Society for Laser Medicine and Surgery Abstracts, Fourteen Annual Meeting, Toronto, Ontario, Canada, p. 48 (Apr. 8-10, 1994).
Goldman, M.P., "Sclerotherapy—Treatment of Varicose and Telangiectatic Leg Veins," Second Edition, Mosby, pp. 454-467 (No Date Given).
Haedersal, et el., "Fractional Nonablative 1540 nm Laser Resurfacing for Thermal Burn Scars: A Randomized Controlled Trial", Lasers in Surgery and Medicine, 41:189-195, 2009, 7 pages.
Johnsson et al., "No photoinactivation of *Propionibacterium acnes* with soft laser treatment," Dermatologica, 175(1):50, 1987.
Kandel, Laurence B., M.D., et al., "Transurethral Laser Prostatectomy in the Canine Model," Lasers in Surgery and Medicine, 12:33-42 (1992).
Kantor et al., "Treatment of acne keloidalis nuchae with carbon dioxide laser," J. Am. Acad. Dermatol., 14:263-267, 1986.
Kelly et al., "Nonablative Laser Treatment of Facial Rhytides: United States Phase II Clinical Study," American Society for Laser Medicine and Surgery Abstracts, p. 38, No date given.
Kilmer et al., "Pulse Dye Laser Treatment of Rhytids," American Society for Laser Medicine and Surgery Abstracts, p. 44 (Apr. 1997).
Korobov et al., "Dependence of the Quantum Yield of Intercombinational Conversion into the Triplet State of Rhodamine 6G on the pH of the Medium", Zhur. Prikl. Spektrosk. 24(1) 28-31 (Jan. 1976).
Krames et al. (2007) "Status and Future of High-Power Light-Emitting Diodes for Solid State Lighting," J. Display Technol., 3(2):160-175.
Leger, J. et al., "Geometrical Transformation of Linear Diode-Laser Arrays for Longitudinal Pumping of Solid-State Lasers," IEEE Journal of Quantum Electronics, vol. 28, No. 4, Apr. 1992.
Lesnik et al., "Agents that cause enlargement of sebaceous glands in hairless mice," Arch. Dermatol., 284:100-105, 1992.
Lucchina et al., "Fluorescence photography in the evaluation of acne," J. Am. Acad. Dermatol. 35:58-63 (1996).

Manstein, D., et al., "Fractional Photothermolysis: A New Concept for Cutaneous Remodeling Using Microscopic Patterns of Thermal Injury," Lasers in Surgery and Medicine, 34: 426-438 (2004).
Manuskiatti et al., "Laser hair removal affects sebaceous glands and sebum excretion . . . ," J. Am. Acad. Dermatol., 41:176-180, 1999.
Matsunaga et al., "Effect of pH on Dye-Laser Output Power", J. Appl. Phys. 48(2):842-844 (Feb. 1977).
McCullough, David L., M.D., "Transurethral Laser Treatment of Benign Prostatic Hyperplasia," and "Transurethral Ultrasound-guided Laser-Induced Prostatectomy (TULIP) Procedure): A Canine Prostate Feasibility Study," by Roth, Robert A., M.D., et al., The Journal of Urology, 146:1126-1135 (1991).
McNicholas, T. A., et al., "Interstitial Laser Coagulation of the Prostate: Experimental Studies," SPIE, 1421:30-35 (1991). (From Proceedings of Lasers in Urol., Laparoscopy, and General Surgery, Jan. 21-23, 1991).
Moretti, Michael, "Holmium Boosts Orthopedic Laser Development," Medical Laser Buyers Guide, p. 93 (1992).
Moretti, Michael, "Lasers Improve Prostatectomy Treatment," Medical Laser Buyers Guide, p. 94-96 (1992).
Mostovnikov, V.A. et al., "Recovery of Lasing Properties of Dye Solutions after Their Photolysis," Sov. J. Quantum Electron, 6(9), Sep. 1976, pp. 1126-1128.
Nanni, C.A. et al., "Complications of Carbon Dioxide Laser Resurfacing," Washington Inst. of Dermatol. Surg. 24:315-320 (1998).
Overholt BF et al. "Balloon photodynamic therapy of esophageal cancer: effect of increasing balloon size." PubMed; Lasers Surg Med. 1996, 18(3):248-52.
Panjehpour M et al. "Spectroscopic diagnosis of esophageal cancer: new classification model, improved measurement system." PubMed; Gastrointest Endosc. Jun. 1995; 41 (6):577-81.
Polanyi, Thomas & Tobias, Irwin, Lasers—A Series of Advances, Edited by A.K. Levine, vol. 2, Marcel Dekker, Inc, N.Y., 1968, pp. 400, 402-403 & 422.
Reed J.T. et al., "Treatment of Periorbital Wrinkles," Washington Inst. of Dermatol. Surg. 23:643-648 (1997).
Rosenfeld, H., et al., "Treatment of Cutaneous and Deep Vascular Lesions with the Nd:YAG Laser," Lasers in Surgery and Medicine, 6:20-23 (1986).
Russel et al. "Flash-Lamp-Excited Self-Injection-Seeded Q-Switch Ti:Al2O3 Laser Oscillator," Applied Optics, vol. 35, No. 24 (Aug. 1996).
Schade, W. et al., "Temperature tuned distributed feedback dye laser with high repetition rate", Applied Optics, vol. 29, No. 27, Sep. 20, 1990, pp. 3950-3954.
Schappert et al., "Temperture Tuning of an Organic Dye Laser" Applied Physics Letters 13(4):124-126 (Aug. 15, 1968).
Shuster, "Acne: The Ashes of a Burnt Out Controversy," Acta Derm. Venereol. Suppl. (Stockh), 120:43-46, 1985.
Sigurdsson et al., "Phototherapy of Acne Vulgaris with Visible Light," Dermatology, 194:256-260, 1997.
Spears et al., "Fluorescence of Experimental Atheromatous Plaques with Hematoporphyrin Derivative," J. Clin. Invest, 71:395-399 (1983).
Spotswood, "Novel Use of Fractional Lasers for Scarring Improves Quality of Life for Injured Troops", http://www.usmedicine.com/articles/novel-use-of-fractional-lasers-for-scarring-improves-quality-of-life-for-injured-troops-.html, (Aug. 2012) , U.S. Medicine ISSN: 0191-6246. 4 pages.
Strauss et al., "Skin Lipids and Acne," Annu. Rev. Med., 26: 27-31, 1975.
Sumian et al., "A new method to improve penetration depth of dyes into the follicular duct : . . . ," J. Am. Acad. Dermotol., 41(2) Part 1:172-175, 1999.
Tarasov, L. V., Laser Physics, Translated from Russion by Ram S. Wadhwa, MIR publishers, Moscow, pp. 178-181, Chapter 2, 1983.
Tarijian, et al., "Fractional abalative laser skin resurfacing: A review", Journal of Cosmetic and Laser Therapy, 13:262-264, ISSN 1476/4172. Informa UK Ltd. Sep. 2011, 3 pages.
Vasily, et al., "Non-Ablative Fractional Resurfacing of Surgical and Post-Traumatic Scars", Journal of Drugs in Dermatology, 8(11):998-1005, Nov. 2009, 8 pages.

(56) References Cited

OTHER PUBLICATIONS

Watson, G. M., MS, "Minimally Invasive Therapies of the Prostate," Minimally Invasive Therapy, 1:231-240 (1992).

Wei Tech Ang et al., "Design of All-Accelerometer Inertial Measurement Unit for Tremor Sensing in Hand-Held Microsurgical Instrument," 2003 IEEE International Conference on Robotics and Automation (vol. 2), Taipei, Taiwan, Sep. 14-19, 2003.

Wei Tech Ang et al., "Kalman Filtering for Real-Time Orientation Tracking of Handheld Microsurgical Instrument," 2004 IEEE/RSJ International Conference on Intelligent Robots and Systems (IROS), Sendai, Japan, Sep. 28-Oct. 2, 2004.

Wilson, S.W., "Passive Alignment of a Semiconductor Laser to an Optical Fiber," Universirty of Maryland, Master's Thesis (1995).

Winters, B.H. et al., "Photochemical Products in Coumarin Laser Dyes," Laboratory for Physical Sciences, College Park, MD, 8-26-74.

Yang et al., "Hybrid optoelectronics: A polymer laser pumped by a nitride light emitting diode," Applied Physics Letters 92, Jan. 23, 2008.

Zapka et al. "Pulse Slicing and Pockels Cell Shutters," J. Phys. E: Sci, Instrum., vol. 15 (1982).

Mang, "Effect of Soft Laser Treatment on Wound Healing in the Hamster Oral Mucosa," American Society for Laser Medicine and Surgery Abstracts, Chapters 25, pp. 5-8.

\* cited by examiner

METHOD AND APPARATUS FOR PHOTOTHERMAL TREATMENT OF TISSUE AT DEPTH

CROSS-REFERENCE TO RELATED APPLICATION

This application is a continuation of U.S. patent application Ser. No. 10/465,137 filed Jun. 19, 2003, which claims the benefit of U.S. Provisional Patent Application Ser. No. 60/389,871, filed Jun. 19, 2002, entitled "Method and Apparatus for Subdermal Heating," by G. Altshuler, et al., incorporated herein by reference in their entirety.

BACKGROUND

1. Field of the Invention

This invention relates to methods and apparatus for the photothermal treatment of tissue and, more particularly, to methods and apparatus for photothermal treatment of at least a selected region of tissue located starting at a depth at about the boundary zone of dermal and subdermal tissue and extending therebelow.

2. Description of the Related Art

The benefits of being able to raise and/or lower the temperature in a selected region of tissue for various therapeutic and cosmetic purposes has been known for some time. For instance, heated pads or plates or various forms of electromagnetic radiation, including microwave radiation, electricity, infrared radiation and ultrasound have previously been used for heating subdermal muscles, ligaments, bones and the like to, for example, increase blood flow, to otherwise promote the healing of various injuries and other damage, and for various therapeutic purposes, such as frostbite or hyperthermia treatment, treatment of poor blood circulation, physical therapy, stimulation of collagen, cellulite treatment, adrenergic stimulation, wound healing, psoriasis treatment, body reshaping, non-invasive wrinkle removal, etc. The heating of tissues has also been utilized as a potential treatment for removing cancers or other undesired growths, infections and the like. Heating may be applied over a small localized area, over a larger area, for example to the hands or feet, or over larger regions of tissue, including the entire body.

Since most of the techniques described above involve applying energy to tissue at depth through the patient's skin surface, peak temperature generally occurs at or near the patient's skin surface and decrease, sometimes significantly, with depth. Further, while microwaves or ultrasonic and other acoustic radiation have been used in the past for certain heating treatments at depth, as disclosed in, for example, U.S. Pat. No. 5,871,524 to Knowlton, U.S. Pat. No. 5,769,879 to Richards, et al., U.S. Pat. No. 5,507,790 to Weiss, or U.S. Pat. No. 5,143,063 to Fellner, since such radiation, particularly microwaves, are potentially mutagenic and can otherwise result in cell or systemic damage and, particularly for acoustic sources, are relatively expensive, and may not be practical for large-area treatment, these techniques have had limited use for the heating of tissues.

While optical and near infrared (NIR) radiation (collectively referred to hereinafter as "optical radiation" is generally both less expensive and, being non-mutagenic, safer than microwaves radiation, the use of optical radiation has heretofore not been considered suitable for most applications involving heating of tissue at depth, the term "tissue at depth" as used herein meaning tissue at the border zone of the dermis and hypodermis, some of which tissue may be in the lower dermis, mostly at a depth deeper than 1 mm, and tissue below this border zone to a depth of up to about 50 mm The reason why this radiation has not been considered suitable is because such radiation is both highly scattered and highly absorbed in surface layers of tissue, precluding significant portions of such radiation from reaching the tissue regions at depth to cause heating thereof. In view of the energy losses due to scattering and absorption, substantial optical (including NIR) energy must be applied in order for enough such energy to reach a region of tissues at depth to have a desired effect. However, such high energy can cause damage to the surface layers of tissue, making it difficult to achieve desired photothermal treatments in tissue regions at depth. For these reasons, optical radiation has heretofore had at most limited value for therapeutic and cosmetic treatments on tissue at depth.

Further, while heating of tissue at depth alone is useful for many treatments, there are treatments, for example to relieve pain and stiffness in muscles or joints, where heating in conjunction with massage or other mechanical stimulation, ultrasound or other acoustic stimulation or electrical stimulation of the tissue may also be useful.

Thus, a need exists for improved method and apparatus for photothermal treatment of tissue regions at depth, and in particular for treatment of subdermal regions of tissue, and for method and apparatus for combining heating with stimulation in such regions for various treatments.

SUMMARY OF THE INVENTION

The present invention generally relates to methods and apparatus for photothermal treatment, both therapeutic and cosmetic, of tissue located at depth in a patient's body, as this term has previously been defined. Optical radiation utilized in practicing the invention is at a wavelength or wavelength band which is neither highly scattered in the patient's skin nor highly absorbed by water in tissue so that the maximum quantity of such radiation can reach the treatment region at depth. The wavelength utilized typically is between about 600 nm and about 1850 nm, more preferably between about 800 nm and about 1350 nm, and most preferably between about 1050 nm and about 1250 nm. Other potential ranges for certain depths of tissue are set forth in Table 1. The longer the wavelength, the lower the scattering; however, outside of the indicated bands, water absorption is so high that little radiation can reach tissue at depth. While the tissue to be treated may be a chromophore at the wavelength(s) utilized within the above bands, this is not a limitation on the invention, and absorption by water, and to a lesser extent fat or lipid, in the region is generally sufficient to achieve the desired heating. In some applications, absorption at certain wavelengths can be increased by delivering a suitable chromophore to the treatment region. The optical radiation source utilized may be a monochromatic source, such as a laser or light emitting diode (LED), or may be a wide spectrum source such as a halogen lamp or arc lamp. Where a wide spectrum source is used, filtering or shifting of wavelengths outside the above bands may be performed. The source may also be a pulsed source or a continuous wave (CW) source. Natural light sources such the sun can also be used to practice this invention. Where the source is a pulsed source, the source typically remains over a treatment region for the duration of each pulse, or a train of pulses may be applied. Where the source is a (CW) source, it is typically moved over the surface of the patients skin at a selected rate, the rate of movement determining the dwell time over a given treatment region.

The invention also requires that cooling be applied to the patient's skin surface concurrently with the application of optical radiation thereto. While the radiation reaches the tissue at depth to be treated quickly to begin the heating thereof, cooling propagates as a cold wave protecting tissue above the treatment region and moving the depth of maximum heating further into the skin. Ideally the cooling wave propagates to a depth just above the treatment region, but does not extend to the treatment region at least until sufficient energy has been delivered to the treatment region to effect the desired treatment Cooling may also be applied to the patient's skin prior to the application of radiation thereto to more effectively protect tissue above the treatment region and to more rapidly result in maximum heat being at or near the desired depth. This may also permit higher energy and shorter duration for the radiation source. The head used to apply the radiation may also be used to apply cooling.

Another feature of the invention is that the radiation is applied at low power for an extended time, the time varying with the depth of treatment and with the treatment being performed. For example, the time may vary from approximately 2 seconds to approximately 2 hours for depths of approximately 1 mm to 50 mm respectively. Depending on depth, the treatment being performed and other factors, the power density may vary from approximately 0.2 to 50 W/cm2, more preferably from approximately 0.5 to 20 W/cm2, and most preferably from 0.5 to 10 W/cm2 or 0.5 to 5 W/cm2.

Other advantages, novel features, and objects of the invention will become apparent from the following detailed description of the invention when considered in conjunction with the accompanying drawings, which are schematic and which are not intended to be drawn to scale. In the figures, each identical, or substantially similar component that is illustrated in various figures is represented by a single numeral or notation. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

Non-limiting embodiments of the present invention will be described by way of example with reference to the accompanying drawings in which.

DETAILED DESCRIPTION

Figure 1:
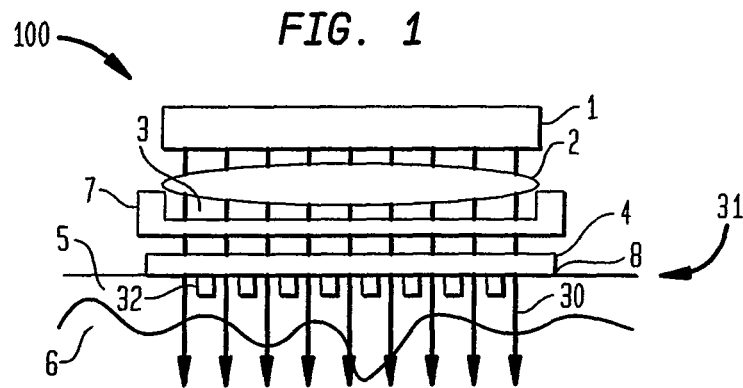
FIG. 1 is a schematic diagram of one embodiment of the invention, as applied to a tissue sample.

Applications in which the invention may be useful include the treatment of various diseases, particularly, cellulite and subcutaneous fat treatment, physical therapy, muscle and skeletal treatments, including relief of pain and stiffness for muscles and joints, and treatment of spinal cord problems, and treatment of cumulative trauma disorders (CTD's) such as carpel tunnel syndrome (CTS), tendonitis and bursitis, fibromyalgia, lymphedema and cancer therapy.

More specifically with respect to cancer therapy, hyperthermia resulting from utilizing the teachings of this invention may be utilized to treat various skin cancers including, but not limited to, basel cell carcinoma, squamous cell carcinoma, lymphoma and possibly treatment (palliative) of melanoma. Hyperthermia may also enhance the efficacy of radiation, for example x-ray, therapy, chemotherapy, therapy with immunmodulators such as ALDARA or PDT therapy. Such combination therapy may for example reduce required treatment time.

The tissue to be treated may be a collagen-rich tissue. Collagen-rich tissues that may be treated include superficial cortical bone, synovium joint capsules, tendon sheaths, menisci, myofascial interfaces, periosteum, fibrotic muscle, or major nerve trunks. The device may also be used for reshaping procedures such as non-invasive wrinkle removal through stimulation of collagen production in a subsurface region of tissue. Heating of the subsurface region of tissue to a temperature of between 37.5 and 45° C. may stimulate generation of new collagen and/or elastin. For example, expression of HSP70 ("Heat Shock Protein") may be stimulated when the tissue is heated to between 41 and 42° C. for between 20 and 30 minutes. Other proteins, cytokins and/or growth factors may also be stimulated or released in response to heating. Significant new collagen deposition, formation or rearrangement may be possible, which may improve skin appearance or texture, allowing wrinkles, fine lines, scars, stretch marks or other indicators to be removed. In general, there exists a relation between the temperature reached and the time of application that is necessary to stimulate new collagen deposition and prevent irreversible damage. Additionally, multiple treatments may be used in some treatment modalities.

Hypothermia resulting from utilizing the teachings of this invention may also be utilized for hair growth management, and for treatment of psoriasis, scars, rosacea and various conditions of toe and finger nails. For hair growth management, which includes temporary and permanent hair removal and control of hair growth, a dermal or subdermal temperature rise of a few degrees, for example to 42-45° C. can produce an anagen effluvium. This could be particularly useful for hair grow management on hairs containing little or no melanin, for example gray, white or blond hairs. The efficacy of such treatment may be enhanced by using wavelengths absorbed by melanin or by performing the treatment in conjunction with other hair removal techniques. Hypothermia may also be used to treat psoriasis, including psoriasis plaques and nail psoriasis. The teachings of this invention may thus be used to treat psoriasis, either alone or conjunction drug treatment, light treatment, for example with an excimer laser, flashlamp, uv or pulse dye laser, or other existing treatment. Scars, having different crosslinking and different denaturation thresholds then normal tissue, may be treated by hypothermia to, for example, reduce turnover, turnover being significantly enhanced for scar tissue. A special handpiece with an aperture adjustable to the shape of the scar may be desirable for treating scars. Hypothermia induced in accordance with the teachings of the invention may also be used to kill demodex mites resident in follicles which cause rosacea. Finally, hypothermia induced by this invention may be used to enhance or control growth rate of toe or finger nails or to otherwise treat conditions of these nails, for example nail fungus and dystrophic nails. The nail (matrix) is relatively accessible to light treatment. The nails can be cooled by emergence in a water bath and exposed to the light. The mechanism for enhanced nail growth may be enhanced metabolism, blood supply (vasodialation by heat and light) or biostimulation.

The application of thermal energy to tissue may also be used, for example, in physical therapy treatments, such as to enhance or accelerate wound healing or relieve pain. Beneficial effects may include a decrease in joint stiffness, an increase in joint extensibility of collagenous structures such as tendons and scar tissue, pain relief, blood-flow changes, or a decrease in muscle spasm and increase in muscle tone. As another example, large protein molecules may have high absorption coefficients, and the heating of protein-rich collagenous tissues may contribute to healing. A wide variety of conditions may be treated using this invention, for example, but not limited to, strained tendons, tenosynovitis, torn ligaments, tendonitis, bursitis, torn joint capsules, or torn muscles. As yet another example, other processes may be activated or deactivated within the tissue during heating. For example, heating of the tissue may be used to enhance or modify the activity of a pharmaceutical or another bioactive substance or to facilitate the delivery thereof through the skin. Mechanical or electrical stimulation, such as massage, may be used in conjunction with heating to achieve benefits greater then can be achieved by either alone. Pressure may also be applied to the skin surface above the treatment region to facilitate the treatment.

In another example, when tissue is heated to greater then the damage temperature of the tissue, irreversible changes to the tissue may occur, up to and including cell death, apoptosis or the like. The damage temperature is the temperature by which cells, collagen, or other tissue components may be irreversibly damaged. The damage temperature may be useful in certain therapeutic situations, for example, to damage unwanted cells or other structures, such as collagen, malignant or benign tumors, hair bulb, deep pigmented lesions or fat. Further, by heating tissue to a temperature above the body temperature (typically 37° C.), but below the damage temperature, it may be possible to change the dynamics of various biological processes, such as metabolism.

Where the tissue is a tumor, it may be desired to use heat in accordance with the teachings of this invention to kill the tumor, or at least a portion thereof, such as a necrotic center. Where the tissue is an artificially created tissue, such as a tissue-engineered scaffold, preferential heating of the center of the artificial tissue may be used, for example, to stimulate cell division within the tissue, to promote cell division or cell growth within the artificial tissue structure.

In certain embodiments, the present invention may be used for non-invasive or non-destructive reduction of localized fat deposits. For example, the invention may be used to heat fat or adipose cells past their damage temperature, causing cell damage and/or necrosis. Alternatively, the treated cells may undergo apoptosis, resulting in cell death. The dead cells may then be removed or resorbed into the body, for example, by the body's phagocytic or lymphatic systems. Fat reduction may also be achieved by heating fat or adipose cells to an elevated temperature, but below the damage temperature. For example, the fat cells may be heated to a temperature of between about 41° C. and about 45° C. Under these conditions, applying heat to subcutaneous fat may activate lipases or metabolize lipids contained within the adipose tissue found within the subcutaneous fat layer, or blood flow may increase to the heated area. Additionally, "lipolysis," or the process of breaking down fat in the body, may be regulated by enzymes sensitive to temperature, such as HSL ("hormone-sensitive lipase"). Thus, elevating the temperature of the adipose cells may increase the lipolysis rate, and thus contribute to a reduction in subdermal fat in the area being treated. This temperature can be below the temperature for vascular/lymph damage so damaged fatty cells and fatty acids can be easily removed from the treatment region. Additionally, application of the present invention may be used in combination with other fat-reduction techniques, such as medication, exercise, or adrenergic stimulation Heating of subcutaneous fat may also result in increased dermal thickness. Thus, fatty tissue may be replaced by fibrous and dermal tissue, this resulting in improved skin appearance. Thermal activation of lymph systems in subcutaneous fat can also be used to treat cellulite by removing proteins from extra cell spaces.

Stated another way, fat and/or cellulite reduction may be achieved utilizing the teachings of this invention by providing an elevated (but below damage threshold ~43-48° C.) temperature in the targeted region at depth. The mild hyperthermia initiates biological response through one or several of the following pathways:

1. Increase of activity of enzymes regulating the process of lipolysis, in particular, hormone sensitive lipase (HSL). As a result, decrease of fat stores in hypodermis.
2. Stimulation of blood and lymph flow in the targeted area with multiple positive consequences, including (but not limited to) further decrease in the fat stores and accelerated regeneration of connective tissue.
3. Induction of apoptosis in adipocytes, with subsequent removal of residual cell material by the body's scavenging system.
4. Decrease of lipid's viscosity, resulting in increasing mobility of fat globules and permeability of adipocytes' membranes.
5. Stimulation and or reorganization of the connective tissue surrounding subdermal fat depots with or without concurrent changes of the dermal collagen.

The net result is a shift of balance between fat and connective tissue in hypodermis toward the latter and improved appearance of skin.

FIG. 1 shows an apparatus 100 for one embodiment of the invention. For this apparatus, optical energy 30 from a suitable energy source 1 passes through optical (for example, focusing) device 2, filter 3, cooling mechanism 4 and contact plate 8, before reaching tissue 31. A suitable optical impedance matching lotion or other suitable substance would typically be applied between plate 8 and tissue 31 to provide enhanced optical and thermal contact. Tissue 31, as shown in FIG. 1, is divided into an upper region 5, which, for applications where radiation is applied to the skin surface, would be the epidermis and dermis, and a lower region 6 which would be a subdermal region in the previous example. Energy 30, possibly in conjunction with one or a combination of focusing from optical device 2, and wavelength selection from filter 3, and with cooling from mechanism 4, results in maximum heating occurring at a selected depth in tissue 31, which depth is, as previously indicated, at or near the junction of regions 5 and 6 or in lower region 6 for this invention. In some embodiments of the invention, certain of these components, such as, for example, filter 3 where a monochromatic source is utilized or optics 2, may not necessarily be present.

In some embodiments of the invention, energy source 1, optical device 2 and/or filter 3 may also require a cooling mechanism. This cooling mechanism may or may not be the same as or connected to cooling mechanism 4 that cools tissue 31 through contact plate 8, as indicated by arrows 32 in FIG. 1. For example, in the embodiment shown in FIG. 1, cooling mechanism 7, shown separately from cooling mechanism 4, is used to cool filter 3. Energy source 1 may be any suitable optical energy source able to produce optical energy 30 at a wavelength that produces heating within tissue 31 at the depth of a desired treatment region. The exact energy source, and the exact energy chosen, may be a function of the tissue 31 to be heated, the depth within the tissue at which treatment is desired and of the absorption of that energy in the desired area to be treated. For example, energy source 1 may be a radiant lamp, a halogen lamp, an incandescent lamp, a arc lamp, a fluorescent lamp, a light emitting diode, a laser (including diode and fiber lasers), the sun or other suitable optical energy source.

Energy source 1 may produce electromagnetic radiation, such as near infrared or visible light radiation over a broad spectrum, over a limited spectrum or at a single wavelength, such as would be produced by a light emitting diode or a laser. In certain cases, a narrow spectral source may be preferable, as the wavelength(s) produced by the energy source may be targeted towards a specific tissue type or may be adapted for reaching a selected depth. In other embodiments, a wide spectral source may be preferable, for example, in systems where the wavelength(s) to be applied to the tissue may change, for example, by applying different filters, depending on the application.

As previously indicated, in order to minimize both scattering and absorption of the applied optical radiation, the optical radiation produced by energy source 1 should be radiation with a wavelength which is minimally scattered and absorbed, the available wavelengths decreasing with increasing depth as generally indicated in Table 1.

Certain wavelengths may be preferentially absorbed by the tissue to be treated. As one example, if the tissue to be treated includes subcutaneous fat, certain wavelengths may be absorbed more effectively by the fat or adipose cells than by the surrounding tissues. For example, optical radiation having wavelengths around 925 nm, 1206 nm, 1730 nm and 2300 nm may be desirable (see for example copending application Ser. No. 09/277,307, which is incorporated herein by reference, for suitable ranges); however, only the lower three of these ranges would typically provide sufficient penetration for use in practicing this invention. Using electromagnetic radiation of these wavelengths, the coefficient of absorption by this radiation in the lipids, and in particular the triglycerides located within the adipose tissue may be greater than that of the absorption coefficient of these wavelengths in water. Thus, these wavelengths when applied to a tissue sample, will preferentially be absorbed by the fat tissue, thus resulting in the preferential heating of this tissue. The selective heating of the fatty tissue can be enhanced by the lower heat capacity of fatty tissue vs. aqueous tissue. Also, the decreased blood perfusion of the subcutaneous fat vs. the dermis can be used to enhance selective heating of the fatty tissue. Compression sufficient to reduce blood flow within the target area can minimize unwanted heat convection, and therefore heat leakage, from the target area. The compression to the subdermal target area can be made selective by forming a skin fold and applying skin pressure sidewise. This results in compression of the subcutaneous fat and of skin outside the field of optical exposure. The skin on top of the skin fold, which skin is exposed to the optical radiation, is not compressed, and therefore the blood flow therein is not appreciably reduced so long as the length of the skin fold does not exceed a critical length. Blood flow within the part of the dermis exposed to optical radiation can help to remove unwanted excessive heat in this skin component.

Where optical device 2 is a focusing device, it may be any suitable device able to focus at least a portion of energy 30 arriving from energy source 1 at tissue 31, and in particular at a selected depth in tissue 31. For example, device 2 may include mirrors, prisms, reflectors, lenses such as Fresnel lenses, collimating lenses or focusing lenses, diffraction gratings, or other optical device.

Filter 3 may be any suitable filter able to select, or at least partially select, certain wavelengths or wavelength bands from energy source 1. In certain types of filters, a specific set of wavelengths may be blocked by the filter. It is also possible that undesired wavelengths in the energy from source 1 may be wavelength shifted in ways known in the art so as to enhance the energy available in the desired wavelength bands indicated above and in Table 1. Thus, filter 3 may include elements designed to absorb, reflect or alter certain wavelengths of electromagnetic radiation. For example, filter 3 may be used to remove certain types of wavelengths that are absorbed by surrounding tissues. For instance, dermis and epidermis tissues are primarily composed of water, as is much of the rest of the human body. By using a filter that selectively removes wavelengths that excite water molecules, the absorption of these wavelengths by the body may be greatly reduced, which may contribute to a reduction in the amount of heat generated by light absorption in these molecules. Thus, by passing radiation through a water-based filter, those frequencies of radiation which may excite water molecules will be absorbed in the water filter, and will not be transmitted into tissue 31. Thus, a water-based filter may be used to decrease the amount of radiation absorbed in tissue above the treatment region and converted into heat.

In other embodiments, filter 3 may be combined with other elements of the device, for example, cooling system 4 or cooling mechanism 7. Thus, water may both attenuate energy 30 arising from energy source 1, as well as cool the contact plate, and tissue in contact with the contact plate, or various other components of the device. More than one filter or filter type may also be present.

FIG. 1 shows a cooling mechanism 4 adjacent to the surface of tissue 31. Cooling mechanism 4 may be any suitable cooling mechanism able to reduce the temperature of tissue 31. Heat energy 32 may be drawn from tissue 31 across contact plate 8 into cooling mechanism 4. For example, cooling system 4 may be air or other suitable gas that is blown over contact plate 8, cooling water, or a cooling oil or other fluid. Mixtures of these substances, such as an oil and water mixture, may also be envisioned. Cooling mechanism 4 may have any suitable configuration, for example, a flat plate, a series of conducting pipes, a sheathing blanket, or a series of channels for the passage of air, or other gases, or liquid across plate 8. For example, in one embodiment, cooling system 4 may be a water-cooled contact plate. In another embodiment, cooling mechanism 4 may be a series of channels carrying a coolant fluid or a refrigerant fluid (for example, a cryogen), which channels are in contact with tissue 31 or with plate 8. In yet another embodiment, cooling system 4 may comprise a water or refrigerant fluid (for example R134A) spray, a cool air spray or air flow across the surface of tissue 31. In other embodiments, cooling may be accomplished through chemical reactions (for example, endothermic reactions), or through electronic cooling, such as Peltier cooling. In yet other embodiments, cooling mechanism 4 may have more than one type of coolant, or cooling mechanism 4 and/or contact plate 8 may be absent, for example, in embodiments where the tissue is cooled passively or directly, for example, through a cryogenic or other suitable spray. Sensors or other monitoring devices may also be embedded in cooling mechanism 4, for example, to monitor the temperature, or determine the degree of cooling required by tissue 31, and be manually or electronically controlled.

In certain cases, cooling mechanism 4 may be used to maintain the surface temperature of tissue 31 at its normal temperature, which may be, for example, 37 or 32° C., depending on the type of tissue being heated. In other embodiments, cooling mechanism 4 may be used to decrease the temperature of the surface of tissue 31 to a temperature below the normal temperature of that type of tissue. For example, cooling mechanism 4 may be able to decrease the surface temperature of tissue 31 to, for example, a range between 25° C. and −5° C.

In some embodiments of the invention, such as shown in FIG. 1, energy 30 from energy source 1 may pass through cooling mechanism 4. In these types of configurations, cooling mechanism 4 may be constructed out of materials able to transmit at least a portion of energy 30, for example, air, water or other gases or fluids, glass, or a clear plastic. In other embodiments, cooling mechanism 4 may be formed out of a series of discrete channels, and energy 30 may pass between these channels. In other embodiments of the invention, energy 30 may not be directed through cooling mechanism 4. For example, in the embodiment shown in FIG. 8, energy source 19 and cooling system 18 may be positioned on opposite sides of chamber 17.

Contact plate 8 may be made out of a suitable heat transfer material, and also, where the plate contacts tissue 31, of a material having a good optical match with the tissue. Sapphire is an example of a suitable material for plate 8. In some embodiments, contact plate 8 may have a high degree of thermal conductivity, for example, to allow cooling of the surface of the tissue by cooling mechanism 4. In other embodiments, contact plate 8 may be an integral part of cooling mechanism 4, or be absent. Contact plate 8 may be made out of a deformable or viscoelastic material in some embodiments of the invention, for example, a gel such as a hydrogel. In other embodiments, contact plate 8 may be made of a solid material, such as a glass, a crystal such as sapphire, or a plastic. In some embodiments of the invention, such as shown in FIG. 1, energy 30 from energy source 1 may pass through contact plate 8. In these configurations, contact plate 8 may be constructed out of materials able to transmit at least a portion of energy 30, for example glass, sapphire, or a clear plastic, or contact plate 8 may be constructed in such a way as to allow at least a portion of energy 30 to pass through contact plate 8, for example, via a series of holes within contact plate 8.

In certain embodiments of the invention, various components of system 100 may require cooling. For example, in the embodiment shown in FIG. 1, optical device 2 and filter 3 may be cooled by cooling mechanism 7. The design of cooling mechanism 7 may be a function of the components used in the construction of the apparatus. Cooling mechanism 7 and cooling mechanism 4, in FIG. 1, are illustrated as separate systems. However, in other embodiments, cooling mechanism 7 and cooling mechanism 4 may be part of the same system, or one or both may be absent. Cooling mechanism 7 may be any suitable cooling mechanism known in the art, such as air, water, or an oil. Mixtures of these substances, such as an oil and water mixture, may also be envisioned. Cooling of the components may be accomplished through convective or conductive cooling.

One or more of energy source 1, optical device 2, filter 3, cooling mechanism 4, or cooling mechanism 7 may be electronically controlled. For example, sensors embedded in cooling mechanism 4 or contact plate 8 may determine the amount of energy reaching tissue 31, and may direct energy source 1 to produce more or less energy or may direct cooling mechanism 4 to increase or decrease cooling, depending on the application. Other sensors and the like may be embedded in any of the components illustrated herein. The controls may be, for example, electronically preprogrammed, or manually operable.

Figure 8:
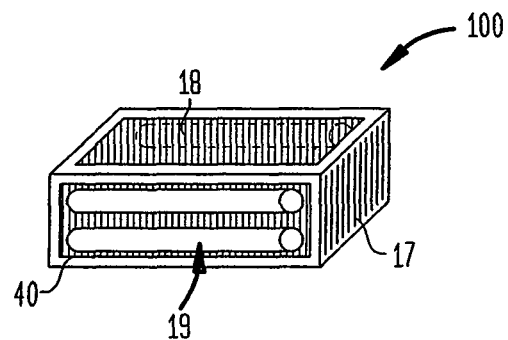
FIG. 8 is a schematic diagram of another embodiment of the invention, showing yet another internal design configuration.
Figure 9:
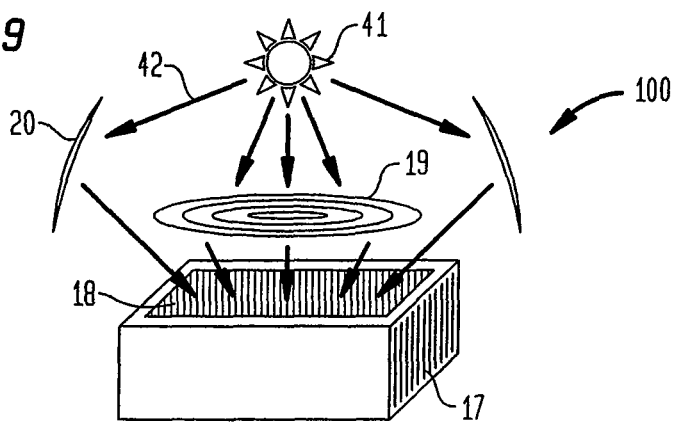
FIG. 9 is a schematic diagram of another embodiment of the invention having a different configuration.

The present invention is not limited to treating a specific region or area of tissue. For example, as illustrated in FIGS. 8 and 9, the invention may be constructed in such a way as to treat an entire person. For example, in FIG. 8, chamber 17 contains cooling mechanism 18 and energy source 19. Cooling mechanism 18 may be cooled in the same ways described above for cooling mechanisms 4 and 7. Energy source 19 may contain, for example, a series of lamps or other energy sources, optionally surrounded by filters 40. In this embodiment, filters 40 are built into the side of chamber 17. FIG. 9 shows another design, where chamber 17 has a cooling mechanism 18, but does not contain an energy source. Instead, energy 42 from the sun 41 or another energy source, such as an external lamp, is directed to chamber 17, for example, directly, by means of reflectors 20, or by means of a lens such as Fresnel lens 19. The patient may be cooled within the chamber by air flow or other suitable cooling mechanism 18.

Figure 2:
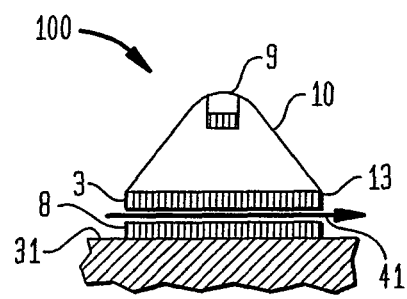
FIG. 2 is a schematic diagram of another embodiment of the invention, showing an internal design configuration.
Figure 3:
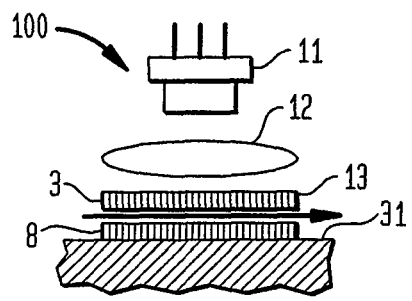
FIG. 3 is a schematic diagram of another embodiment of the invention, showing another internal design configuration.

In FIG. 2, another embodiment of the invention is shown. In this embodiment, a lamp 9, for example an incandescent lamp, is used as the energy source. Lamp 9 is surrounded by a specially coated reflector 10 to maximize light delivery efficiency to the treatment region of tissue 31. A fluid 13 may pass between contact plate 8 and filter 3. Contact plate 8, cooled by fluid 13, may cool the surface of the tissue to which it is applied. In FIG. 3, lamp 9 has been replaced by a monochromatic light emitting element 11 and lens 12, element 11 being, for example a laser diode, other suitable laser or a light emitting diode. As in the embodiment shown in FIG. 2, contact plate 8 and filter 3 are cooled by fluid 13 flowing therebetween; these two components may also be cooled by flow of cold liquid gas, for example R134A, from a pressurized can. Thus, this embodiment illustrates how a monocromatic element 11 may be used as the energy source.

Figure 4:
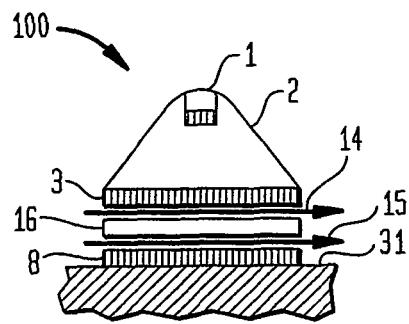
FIG. 4 is a schematic diagram of another embodiment of the invention, showing another internal design configuration.
Figure 5:
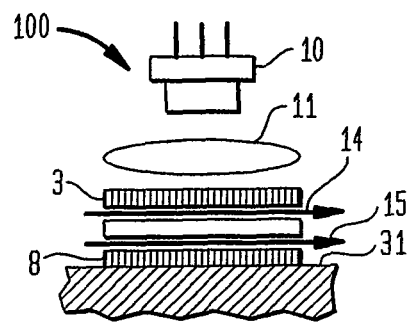
FIG. 5 is a schematic diagram of another embodiment of the invention, showing another; internal design configuration

A different type of cooling mechanism is illustrated in FIG. 4. In FIG. 4, energy arising from energy source 1 is reflected using reflector 10 through filter 3, a transparent isolating material 16, and contact plate 8. Two fluids are used to cool the filter and the contact plate. Upper fluid 14 flows between filter 3 and isolating material 16, while lower fluid 15 passes between isolating material 16 and contact plate 8. Fluids 14 and 15, in this embodiment, may not be the same fluid; however, in other embodiments, the two fluids may be the same fluid, or have a common reservoir. Contact plate 8, in this embodiment, may be made out of, for example, a transparent or a semi-transparent material, such as a glass, plastic or sapphire. Alternatively, contact plate 8 may be formed out of an opaque material, but have openings to allow energy to pass through contact plate 8. A similar embodiment of the invention is shown in FIG. 5, where the energy source 1 has been replaced by an element that produces discrete wavelengths, such as a light emitting diode or a laser diode 11. Optional lens 12 has also been added to the system as illustrated in FIG. 5.

Figure 6:
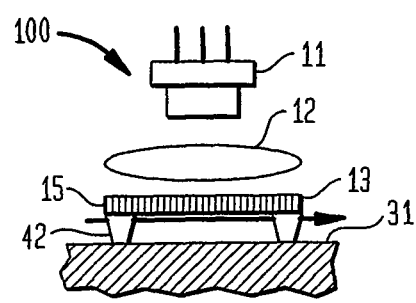
FIG. 6 is a schematic diagram of another embodiment of the invention, showing another internal design configuration.

In certain embodiments of the invention, contact plate 8 may be absent. For example, in the embodiment shown in FIG. 6, no contact plate is used, and fluid 13 (for example a liquid, gas such as air or a spray) passes or flows directly over the surface of tissue 31. Legs 42 connected to the device may be constructed in such a manner as to correctly position filter 3 over the surface of the tissue. Legs 42 may be any component able to maintain a proper distance between the surface of tissue 31 and device 100. In some embodiments of the invention, legs 42 may be constructed out of a flexible or a semi-solid substance that, for example, may conform to the surface of tissue 31, such as a gel. In other embodiments of the invention, legs 42 may be constructed out of a solid substance, such as rubber or plastic. Legs 42 may have any arrangement underneath the device that allows for the proper positioning of the device relative to the tissue. For example, legs 42 may be arranged in a triangular or a square pattern. In other embodiments of the invention, legs 42 may be a ring or a series of bars that surrounds the area being treated or legs 42 may be absent.

Figure 7:
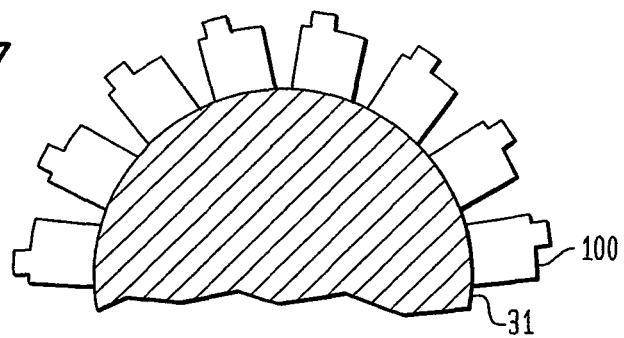
FIG. 7 is a schematic diagram illustrating a plurality of devices of the invention being used in conjunction with each other.

More than one device 100 of this invention may be used simultaneously. For example, in FIG. 7, a series of devices 100 have been arranged into a semicircular pattern. These devices may be linked together to treat large areas of a subject's body. Additionally, the devices may be interconnected in such a way as to provide flexibility, so that, for example, the apparatus may conform to the contours of the body. For example, the device may be worn as a belt, a leg wrap, an arm wrap, or wrapped around the torso. Devices 100 may also be mounted to a chair, bed or other suitable surface for the treatment of a patient's back, thighs and/or buttocks. Alternatively, devices 100 may be used to create an array of small island areas within a larger area (see for example copending application Ser. No. 10/033,302 which is incorporated herein by reference). This may, for example, be a safer alternative to large area heating, particularly for extended treatment regimens. By optimizing the spacing between treated areas, for example, through the addition of "masks" in filter 3 between energy source 1 and tissue 31 that block portions of the energy arising from energy source 1, and/or through the use of multiple separate devices 100 as is shown in FIG. 7, treatment of the subdermal tissue may be maximized, while causing a minimal amount of patient discomfort, and/or allowing faster recovery time.

Where optical source 1 is a continuous wave (CW) or other long duration source, device 100 for various of the embodiments may be slid or scanned over the surface of the patient's skin to overlie successive treatment regions, the dwell time, and thus the treatment duration, for each such region being a function of the rate at which the device is moved The device may also include a cooling mechanism ahead of the portion of the device under source 1 to precool skin above the treatment region (see for example issued U.S. Pat. Nos. 6,273,884 and 6,511,475, which are incorporated herein by reference).

Any of the embodiments can include a contact sensor to assure good optical and thermal coupling, and systems operating in the sliding mode may also include one or more motion sensors to control radiation delivery, cooling and other functions dependent on scanning speed, to enhance system safety and for other reasons.

In addition to coupling the deep heating treatment of this invention with deep cooling to enhance treatment of fat, bone, muscle, etc., device 100 may also include a massager, vibrator or other mechanical stimulation device or a DC or other suitable electrical stimulation source. It has been found that such mechanical or electrical stimulation is more effective for hot tissue. Similarly, the effect of deep heating may be enhanced by massage or other stimulation because both heat and cold generally penetrates better in compressed skin and subdermal tissue. Thus, the combination of deep heating and mechanical or electrical stimulation may provide significantly better results then either one alone. Heating may also be enhanced by supplementing the optical heating with, for example electro-stimulation by AC/DC, or additional heating by RF, etc. Tensioning or pressure applied to the skin overlying the treatment region may also enhance treatment effect.

The teachings of this invention may also be utilized for hair removal treatments by targeting the hair bulb, which is generally located in the subcutaneous layer 6. The treatment would be done at low power sufficient to raise the temperature of the fat surrounding the hair bulb, and thus the hair bulb, to roughly 45° C. and should be performed for a relatively long time period, for example, 15 minutes. The hair bulb also contains high proliferation water cells which react strongly with the applied radiation to increase bulb temperature, leading to the destruction thereof.

The function and advantages of these and other embodiments of the present invention will be more fully understood from the following examples. These examples are intended to be only illustrative in nature and are not intended to limit the scope of the invention.

EXAMPLE 1

This example illustrates theoretical calculations corresponding to one embodiment of the invention as applied to human skin.

Figure 10:
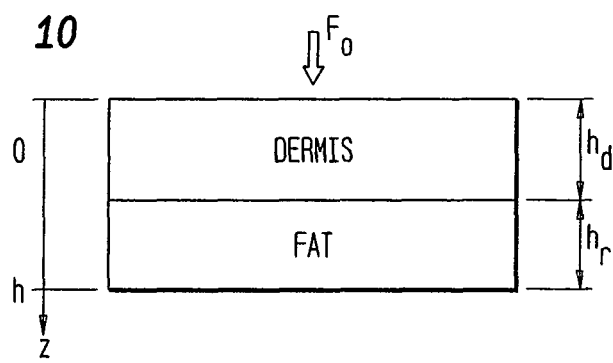
FIG. 10 is a schematic drawing of a model of tissue, used in certain calculations.

Initially, a model of the skin was prepared. This model included two layers of tissue possessing distinct optical and thermal properties: dermis and subcutaneous fat (FIG. 10). The presence of fine structures such as the basal layer and the vessel plexus was neglected. Monochromatic light was assumed to be incident normal to the surface. The input power density was designated as $F_0$. Both the surface temperature $(T_s)$ at depth $z=0$ and the bottom temperature $(T_h)$ at depth $z=h$ were kept fixed at prescribed levels. Specifically, $T_h$ was set at 37° C. due to the temperature stabilization effect of blood and metabolic heat generation on muscle tissue. The objective of this example was to evaluate the steady-state temperature distribution within the skin and to find the characteristic depth $z_{max}$ where the steady-state temperature reaches a maximum.

Starting with the problem of light transport within the tissue, scattering in both tissue layers predominated strongly over absorption, allowing the diffuse approximation to be applied. This approach was particularly valid within the wavelength range of 600 nm to 1400 nm, which may also be referred to as the "therapeutic window". The one-dimensional light transport problem in the diffusion approximation for the two-layered tissue model of FIG. 10 can be solved assuming both the tissue irradiance and the light flux to be the continuous functions of coordinate z at the dermis and fat interface. The resulting expression for the tissue irradiance, $\psi$, obtained may be written in the following general form:

$$\psi_1(z) = F_0 \cdot \tau_{col}' [V_1 \cdot \exp(-\kappa_1 z) + V_2 \cdot \exp(\kappa_1 z) - V_3 \cdot \exp(-\mu t_1 z)], \quad z \le h_d,$$
$$\psi_2(z) = F_0 \cdot \tau_{col}' [V_4 \cdot \exp(-\kappa_2 (z-h_d)) - V_5 \cdot \exp(-\mu t_2 (z-h_d))], \quad z > h_d, \quad (1)$$

where indices 1 and 2 stand for dermis and subcutaneous fat, respectively. $\kappa=\sqrt{3\cdot\mu_a\cdot\mu_{tr}}$ and $\mu t=\mu_a+\mu_s$ are the diffusion and extinction coefficients for light in the corresponding layers, and $$\tau_{col} = \frac{4n_1 n_2}{(n_1 + n_2)^2}$$

is the attenuation coefficient of the collimated light at the surface. Flux amplitudes $V_1$ to $V_5$ were determined by the boundary and interface conditions. In particular, if the coefficients of refraction of both layers are the same, the interface condition at $z=h_d$ is such that both the radiance and the total light flux should be continuous functions of depth.

Turning to the problem of heat conduction within the two-layered tissue model, the time dependent equation of heat conduction in the k-th layer was:

$$\frac{\partial}{\partial t}T(z,t) = \alpha_k \frac{\partial^2}{dz^2}T(z,t) + Q_k(z,t), \tag{2}$$

yielding the following steady-state equation:

$$\alpha_k \frac{d^2}{dz^2}T(z) = -Q_k(z), \tag{3}$$

where $\alpha_k$ was the thermal diffusivity of the k-th layer (k=1,2). The heat source term $Q_k$ in these equations describes the generation of heat due to light absorption in the tissue. In the steady-state case, the source term is:

$$Q_k(z) = \frac{\mu_{ak}}{\rho_k \cdot c_k} \cdot \psi_k(z), \tag{4}$$

where $\mu_{ak}$, $\rho_k$ and $c_k$ are the coefficient of absorption, density, and specific heat of the k-th layer, respectively.

Boundary conditions were assumed to be $T(0)=T_s$, $T(h)=T_h$. The solution of Equation (3) was then found to be:

$$T_2(z) = T_h + B\cdot(h-z) - \frac{1}{\alpha_2}\cdot\int_z^h dz' \int_{hd}^{z'} dz'' Q(z''), \tag{5}$$

$$T_1(z) = T_s + A\cdot z - \frac{1}{\alpha_1}\cdot\int_0^z dz' \int_0^{z'} dz'' Q(z''),$$

where parameters A and B have to be found from the interface conditions. For the case of perfect thermal contact:

$$T_1(h_d) = T_2(h_d), \tag{6}$$

$$k_1 \frac{d}{dz}T_1(h_d) = k_2 \frac{d}{dz}T_2(h_d),$$

where and $k_1$ and $k_2$ are the thermal conductivities of dermis and fat, respectively.

The analytic expression for the temperature, T(z), was then obtained by substituting Equation (3) into Equations (4) and (5).

A simpler expression for the temperature distribution was obtained for a homogenous medium with no layered structure. In this case, the radiance distribution took the following general form:

$$\psi(z) = F_0 \tau_{col}[\exp(-\mu_t z) + \phi_d(z)], \tag{7}$$

where the first term was the collimated radiance and the second one was the diffuse radiance given by:

$$\phi_d(z) = V_2 \cdot \exp(-\kappa\cdot z) - V_1 \cdot \exp(-\mu_t z). \tag{8}$$

The temperature distribution was:

$$T(z) = \tag{9}$$
$$T_s + (T_h - T_s)\cdot\frac{z}{h} + F_0\frac{V_0}{\alpha}\left\{\frac{1-V_1}{\mu_t^2}\cdot\left[1 - e^{-\mu_t z} - (1 - e^{-\mu_t z})\cdot\frac{z}{h}\right] + \frac{V_2}{\kappa^2}\cdot\left[1 - e^{-\kappa h} - (1 - e^{-\kappa h})\cdot\frac{z}{h}\right]\right\}$$

with $$V_0 = \mu_a \cdot \tau_{sp}/(\rho c).$$

Differentiating Equation (9) with respect to z yields the following implicit expression for the depth zmax, the localized tissue depth at which maximum temperature occurs:

$$T_h - T_s = \frac{F_0 \cdot V_0}{\alpha}\cdot\left[\frac{1-V_1}{\mu_t^2}\cdot(1 - e^{-\mu_t\cdot h} - \mu_t\cdot h\cdot e^{-\mu_t z_{max}}) + \frac{V_2}{\kappa^2}\cdot(1 - e^{-\kappa\cdot h} - k\cdot h\cdot e^{-\kappa z_{max}})\right] \tag{10}$$

Tmax=Th−Ts is maximum temperature rise in the tissue at the depth zmax.

Equation (10) was solved numerically. To get an approximate analytic expression, the inequality $\mu_t \gg \kappa$ was used, which is typically valid within the therapeutic window. Then, dropping the exponential terms with $\mu_t$, and solving the simplified equation with respect to $z_{max}$ yielded the following $$z_{max} = -\frac{1}{\kappa}\cdot\ln\left[\frac{\kappa\cdot(1-V_1)}{V_2\cdot h\cdot\mu_t^2} + \frac{1-\exp(-\kappa h)}{\kappa h} - \frac{\alpha\kappa}{F_0 V_0 V_2 h}\cdot(T_h - T_s)\right]. \tag{11}$$

Maximum temperature can be calculated from (9) as $T_{max}=T(z_{max})$

Figure 11:
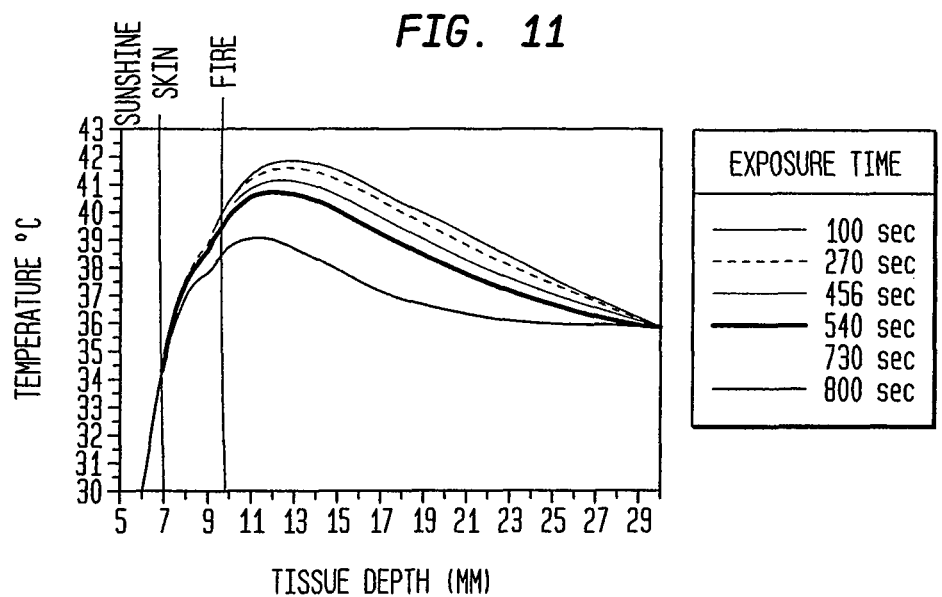
FIG. 11 is a plot of the temperature produced by an embodiment of the invention in a tissue sample versus tissue depth.
Figure 13:
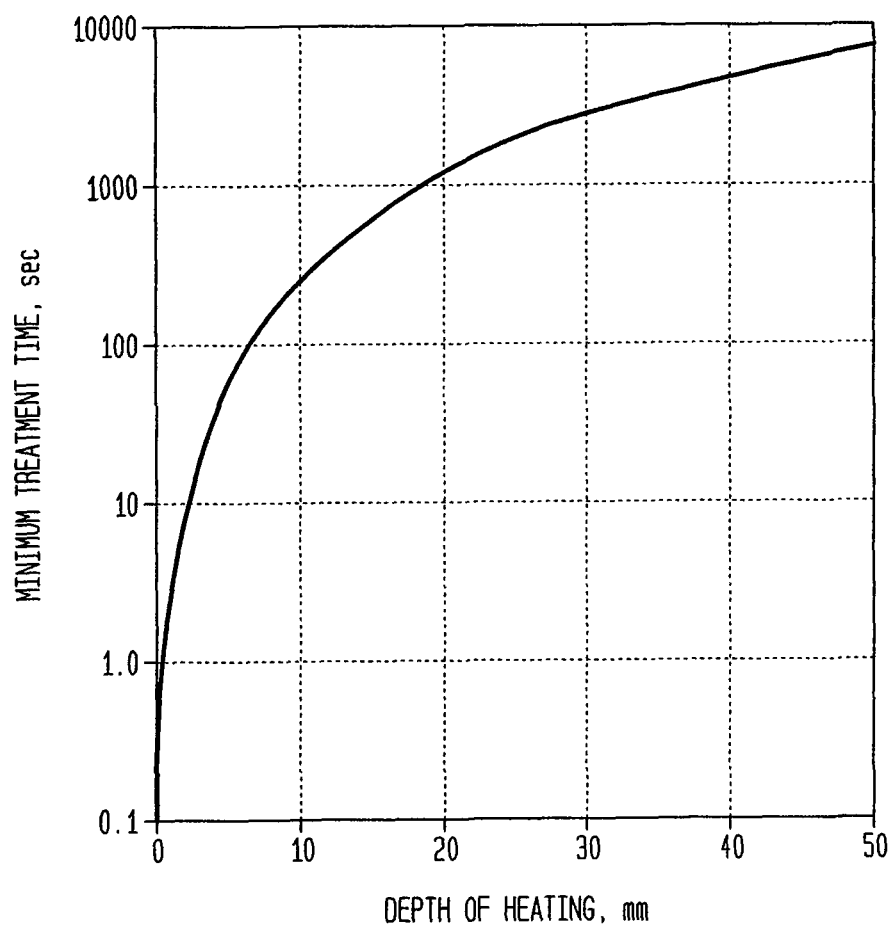
FIG. 13 is a plot of depth of heating vs. treatment time as determined using Equation 12.

It can be seen from these results that an increase in $F_0$ caused the temperature maximum to move upwards, provided the input flux is sufficiently small. At larger value of $F_0$, the maximum ceased to move while proceeding to grow in amplitude. The treatment time should be long enough to remove heat from the layer $0 < z < z_{max}$. This time $t_{min}$ was given by the formula:

$$t_{min} = \frac{(6 \div 60)\cdot z_{max}^3}{\alpha_1\cdot z_1 + \alpha_2\cdot z_2} \tag{12}$$

where $z_1$ is the depth into dermis and $z_2$ is depth into subcutaneous fat, and $z_1+z_2=z$ is depth of treatment. The numerator constant (6÷60) varies within the given range depending on how close the desired temperature is to Tmax, being 6 for Tzmax=90% Tmax and 60 for Tzmax=99% Tmax. The treatment time must be longer than $t_{min}$. FIG. 11 shows a typical temperature distribution in the body. FIG. 13 and Table 2 show minimum treatment time as a function of depth of treatment z.

Equations (10), (11), and (12) describe a set of heating and cooling parameters that allow control of both the value and location of the internal temperature maximum. FIG. 11 shows a graph generated using these equations that shows that a broad spectral source, having a proper set of filters, combined with surface cooling, allows the temperature within the adipose layer of tissue to be elevated to a maximum, while maintaining acceptable temperatures surrounding tissue and in particular, in tissue above the treatment region through which the radiation passes.

Thus, this example illustrates theoretical calculations corresponding to one embodiment of the invention.

EXAMPLE 2

The following prophetic example illustrates treatment parameters for different body layers that may be used in one embodiment of the invention, as applied to human skin.

Based on the calculation illustrated in Example 1, treatment parameters for different layers of the body that may be used in one embodiment of the invention can be determined. These calculations are summarized in Table 1. The body layers model includes the reticular dermis, dermis subcutaneous fat junction, and subcutaneous fat layer.

Using a broad-spectrum lamp in this embodiment of the invention, the treatment parameters include a surface cooling mechanism able to maintain a surface cooling temperature of between 0° C. and 32° C.; a broad-spectrum lamp, where the color temperature of the lamp is between 300 K and 3000 K, with filtering of more than 50% of the light having wavelengths of less than 800 nm and greater that 1800 nm, preferably 900 to 1400 nm, and most preferably 1100 to 1250 nm. Depending on depth, the treatment being performed and other factors, the power may vary from approximately 0.2 to 50 W/cm2, and more preferably from approximately 0.5 to 20 W/cm2, with a treatment time of between 2 sec for a 1 mm depth and 7300 sec for a 50 mm depth When operating in sliding mode, treatment power and duration increase.

Thus, this prophetic example illustrates exemplary treatment parameters that may be used to heat different layers of the body, in one embodiment of the invention.

TABLE 1

Typical parameters of treatment:

| Organ | Depth of peak temperature, mm | Wavelength range, μm | | | Treatment parameters with precooling preferable wavelength range | |
|---|---|---|---|---|---|---|
| | | Maximum | Preferable | Most for preferable | Cooling temperature ° C. | Precooling time, s |
| Reticular dermis | 1-3 | 0.6-1.85 | 0.8-1.4 & 1.5-1.8 | 1.2-1.3 & 1.6-1.8 | 5 | 1-30 |
| Dermis subcutaneous fat junction | 2-5 | 0.6-1.35 & 1.6-1.8 | 1.1-1.25 & 1.65-1.8 | 1.15-1.23 & 1.7-1.75 | 5 | 1-30 |
| Subcutaneous fat | 5-10 | 0.8-1.4 & 1.6-1.7 | 1.1-1.3 & 1.65-1.8 | 1.15-1.23 | 5 | 30-110 |
| | 10-20 | 0.8-1.3 | 1.1-1.25 | 1.15-1.23 | | 110-450 |
| | 20-50 | 0.8-1.3 | 1.05-1.25 | 1.05-1.15 | | 450-2800 |

| Organ | Treatment parameters with precooling for preferable wavelength range | | Treatment parameters without precooling for preferable wavelength range | | |
|---|---|---|---|---|---|
| | Time of treatment, s | Fluence J/cm² | Cooling temperature, ° C. | Minimum time of treatment, s | Power density, W/cm² |
| | | | | | W/cm² |
| Reticular dermis | 2-40 | 10-200 | 5-30 | 5 | 2-65 | 2.5-50 |
| Dermis subcutaneous fat junction | 10-40 | 150-200 | 5-15 | 5 | 2-65 | 2.5-50 |
| Subcutaneous fat | 40-300 | 200-500 | 1.7-5 | 5 | 65-270 | 0.5-20 |
| | 300-800 | 500-1000 | 1.2-5 | 5 | 270-1100 | 0.5-10 |
| | 800-1200 | 1000-1200 | 1-1.2 | 5 | 1100-7300 | 0.2-5 |

TABLE 2

Minimum treatment time without precooling

| Depth, mm | Treatment time, sec |
|---|---|
| 1 | 2 |
| 2 | 10 |
| 3 | 20 |
| 4 | 40 |
| 5 | 65 |
| 6 | 95 |
| 7 | 130 |
| 8 | 170 |
| 9 | 220 |
| 10 | 275 |
| 12 | 400 |
| 14 | 550 |
| 16 | 720 |
| 18 | 915 |
| 20 | 1100 |
| 25 | 1800 |
| 30 | 2600 |
| 35 | 3500 |
| 40 | 4600 |
| 45 | 5900 |
| 50 | 7300 |

EXAMPLE 3

Figure 12:
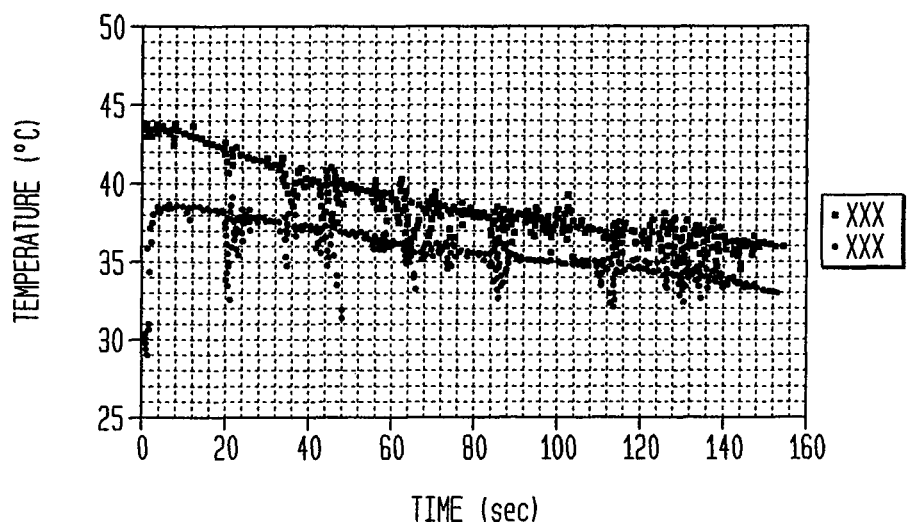
FIG. 12 is a plot of a temperature relaxation profile produced by an embodiment of the invention in a tissue.

In this example, a device 100 of this invention substantially as shown in FIG. 2 was used to heat subcutaneous fat in the stomach region of a volunteer. Light from a halogen lamp 9 was filtered with a combination of a short cut or high pass filter 8 with an 800 nm cut-off and a 3 mm thick water layer 41. The temperature of water 41 was 12° C., while the temperature of a sapphire plate 8 and of the skin interface was 18° C. Power density was 4 W/cm2 and the treatment time was 300 sec. After heating the subcutaneous fat layer for 300 sec., the device was removed, and two thermocouples were immediately implanted 1 mm and 8 mm below the skin surface under the heated region to determine the final, steady-state temperatures and to monitor the temperature relaxation profiles in the dermis and fat layer respectively. Temperature data recorded by the two thermocouples are shown in FIG. 12. The initial temperature of the subcutaneous fat layer at a depth of 8 mm was found to be approximately 45° C., while the temperature of the dermis, 1 mm below the surface of the skin, was found to be about 40° C. and the temperature at the epidermis was 24° C. Over the course of the next several minutes, the temperatures of the dermis and the subcutaneous fat layer decreased towards basal levels of 37° C. for the subcutaneous fat layer and approximately 32° C. for the dermis.

The same device 100 was used to perform the same test on a 25 mm bulk of pig skin and subcutaneous fat which was placed on a thermally stable plate with a temperature of 37° C. The power density for this test was 10 W/cm2 and cooling water having a temperature of 4° C. was used. After a treatment time of 300 sec., peak temperature of 53° C. was found at a depth 14 mm into the fat. The temperature at the epidermis at this time was 38° C. After about 6 weeks, this exposure setting induced reduction of subcutaneous fat without evidence for epidermal damage. A partial replacement of fatty tissue by connective collagen tissue was observed. A reduction of hair growth was also observed several weeks after this and similar exposure settings, even if a lower temperature rise was obtained and only a single treatment was performed. This clearly emphasized the possibility of using this method to manage unwanted hair growth. Highly proliferating cells like sebocytes within the sebaceous glands or hair matrix cells within the hair follicle are particularly sensitive to heating which can be used to achieve selective effects on these structures even by unselective heating of the depth were these structures are located. Hair matrix cells are also surrounded by fatty cells and the sebaceous glands are generating lipids. The decreased heat capacity for lipids provides additional selective effects. This can also be specifically useful for the treatment of non pigmented hairs that are usually not affected by standard light assisted methods for photoepilation based on selective photothermolysis. Hair growth management may include permanent or temporary hair removal or merely controlling/slowing hair growth rate.

These examples thus illustrates how a device of the invention may be used to heat a subdermal layer of tissue to a temperature significantly higher than normal body temperature and the temperature of surrounding tissue, including tissue between the skin surface and the treatment region.

While several embodiments of the invention have been described and illustrated herein, those of ordinary skill in the art will readily envision a variety of other means and structures for performing the functions and/or obtaining the results and/or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention. In the claims, all transitional phrases or phrases of inclusion, such as "comprising," "including," "carrying," "having," "containing," and the like are to be understood to be open-ended, i.e. to mean "including but not limited to." Only the transitional phrases or phrases of inclusion "consisting of" and "consisting essentially of" are to be interpreted as closed or semi-closed phrases, respectively.

The invention claimed is:

1. Apparatus for treating at least a selected region at depth of a patient while protecting tissue above the selected region, comprising:
    an optical radiation source for delivering infrared optical radiation at a power density of between about 0.2 W/cm$^2$ and about 50 W/cm$^2$ to the patient's skin, said power density varying at least in part as a function of the depth of said selected region;
    a water filter to at least attenuate wavelengths from said optical radiation source which are selectively absorbed by water; and
    a cooling mechanism configured to cool tissue.

2. Apparatus as claimed in claim 1 wherein said water filter includes chilled water flowing between said optical radiation source and the patient's body, said flowing chilled water also functioning as part of said cooling mechanism.

3. Apparatus as claimed in claim 1 wherein said optical radiation source provides radiation at least primarily at one or more wavelengths between about 800 nm and about 2300 nm.

4. Apparatus as claimed in claim 3 wherein said source provides radiation at least primarily at one or more wavelengths between about 800 nm and about 1850 nm.

5. Apparatus as claimed in claim 4 wherein said source provides radiation at least primarily at one or more wavelengths between about 800 nm and about 1350 nm.

6. Apparatus as claimed in claim 4 wherein said source provides radiation at least primarily at one or more wavelengths between about 1050 nm and about 1250 nm.

7. Apparatus as claimed in claim 1 wherein said source includes optics for shaping radiation to be delivered to said selected region.

8. Apparatus as claimed in claim 1 wherein said optical radiation source and said cooling mechanism are concurrently operated for a period of at least two seconds.

9. Apparatus as claimed in claim 8 wherein said optical radiation source and said cooling mechanism are concurrently operated for a period of at least five seconds.

10. Apparatus as claimed in claim 8 including a precooling mechanism which cools tissue above said selected region prior to the concurrent operation of said optical radiation source and said cooling mechanism.

11. Apparatus as claimed in claim 10 wherein said cooling mechanism and said precooling mechanism are the same mechanism.

12. Apparatus as claimed in claim 10 wherein said optical radiation power and said period of concurrent operation are based at least in part on said precooling mechanism.

13. Apparatus as claimed in claim 1 wherein said optical radiation source and said cooling mechanism are concurrently operated for a period of between about two seconds and about two hours.

14. Apparatus as claimed in claim 1 wherein said source includes a broadband optical radiation source, and a filter through which radiation from said broadband source is passed, at least 50% of the filtered light having wavelengths between 900 nm and 1400 nm such that said apparatus is an apparatus for fat reduction, said radiation heating subdermal fat tissue.

15. Apparatus as claimed in claim 1 including a stimulation mechanism for stimulating tissue in said selected region.

16. Apparatus as claimed in claim 15 wherein said stimulation mechanism comprises at least one of a vibrator, a massager, a skin tensioning stimulator, acoustic stimulator, and an electrical stimulator.

17. Apparatus as claimed in claim 1 wherein said selected region contains at least one hair bulb, and wherein parameters for said apparatus, including said optical radiation source, are selected to slowly damage said bulb.

18. Apparatus for treating at least a selected region at depth of a patient while protecting tissue above the selected region, comprising:
an optical radiation source for delivering optical radiation at a power density of between about 0.2 W/cm$^2$ and about 50 W/cm$^2$ to the patient's skin, said power density varying at least in part as a function of the depth of said selected region;
a water filter to at least attenuate wavelengths from said optical radiation source which are selectively absorbed by water;
a cooling mechanism configured to cool tissue; and
a mechanism for removing heat from said water filter.

19. A method for treating at least a selected region at depth of a patient's body while protecting tissue above the selected region, comprising:
(a) selectively delivering optical radiation generated by a narrow spectral source at a power density between approximately 0.2 W/cm$^2$ and 50 W/cm$^2$ to the patient's body above said selected region, said power density varying at least in part as a function of the depth of said selected region, said optical radiation being applied to said selected region for at least approximately 2 seconds; and
(b) concurrently cooling patient tissue above said selected region to a temperature below that of the selected region.

20. A method as claimed in claim 19 wherein said power density is between about 0.5 W/cm$^2$ and about 20 W/cm$^2$.

21. A method as claimed in claim 19 wherein step (a) includes filtering said optical radiation before delivering it to said patient's body.

22. A method as claimed in claim 19 wherein said method is a method for performing therapy on at least one of subdermal muscle, ligament and bone, said radiation causing heating of such muscle/ligament/bone and of tissue in the area thereof to at least increase blood flow in such area.

23. A method as claimed in claim 19 wherein said method is a method for treating a selected unwanted growth, said radiation heating said growth sufficiently to cause the destruction thereof.

24. The method of claim 19, wherein the electromagnetic energy is at least primarily at one or more wavelengths between about 600 nm and about 1850 nm.

25. The method of claim 24, wherein the electromagnetic energy is at least primarily at one or more wavelengths between about 800 nm and about 1350 nm.

26. The method of claim 24 wherein the electromagnetic energy is at least primarily at one or more wavelengths between about 1050 nm and about 1250 nm.

27. The method of claim 19 wherein step (a) and step (b) are performed concurrently for a period of at least two seconds.

28. The method of claim 27 wherein step (a) and step (b) are performed concurrently for a period of at least five seconds.

29. The method of claim 19 wherein step (a) and step (b) are performed concurrently for a period of between about two seconds and about two hours.

30. The method of claim 19 including the step of precooling tissue above said selected region.

31. The method of claim 30 wherein said optical radiation power and a period of said concurrent operation are based at least in part on said precooling step.

32. The method of claim 19 wherein said selected region is heated during step (a).

33. The method of claim 19 including the step of stimulating tissue in said selected region.

34. The method of claim 33 wherein said step of providing stimulation provides at least one of vibrating stimulation, massaging stimulation, skin tensioning, acoustic stimulation and electrical stimulation.

35. The method of claim 19 wherein said selected region contains at least one hair bulb, and wherein parameters for said method, including said radiation, are selected to slowly damage said bulb.

36. A method for treating at least a selected region at depth of a patient's body while protecting tissue above the selected region, comprising:
(a) selectively delivering radiation to the patient's body above said selected region to heat the region;

(b) concurrently cooling patient tissue above said selected region to a temperature below that of the selected region; and (c) applying at least one of vibrating, massaging, skin tensioning, acoustic and electrical stimulation to said region.

37. The method of claim 19, further comprising:

(c) applying at least one of vibrating, massaging, skin tensioning, acoustic and electrical stimulation to said region.

38. The method of claim 19, wherein said method is a method for performing at least one of wrinkle removal, pain treatment, and cellulite treatment.

39. The method of claim 19, wherein said narrow spectral optical radiation source is a monochromatic source.

40. The method of claim 19, wherein said narrow spectral optical radiation source is a laser.

41. The method of claim 40, wherein said laser is a fiber laser or a diode laser.

42. The method of claim 19, wherein said narrow spectral optical radiation source is an LED.

43. A method for treating at least a selected region at depth of a patient's body while protecting tissue above the selected region, comprising:

(a) selectively delivering optical radiation at a power density between about 0.5 W/cm$^2$ and about 5 W/cm$^2$ to the selected region, said optical radiation being applied to said selected region for at least approximately 2 seconds; and (b) concurrently cooling patient tissue above said selected region to a temperature below that of the selected region.

44. Apparatus for treating at least a selected region at depth of a patient while protecting tissue above the selected region, comprising:

a narrow spectral optical radiation source for delivering infrared radiation at a power density of between approximately 0.2 W/cm$^2$ and 50 W/cm$^2$ to the patient's skin for a duration between two seconds and two hours, both said power density and said duration increasing with increased depth for said selected region; and a cooling mechanism for cooling tissue above said selected region to a temperature below that of said selected region.

45. The apparatus of claim 44, wherein said optical radiation source provides radiation at least primarily at one or more wavelengths between about 800 nm and about 2300 nm.

46. The apparatus of claim 44, wherein said optical radiation source provides radiation at least primarily at one or more wavelengths between about 800 nm and about 1850 nm.

47. Apparatus for treating at least a selected region at depth of a patient while protecting tissue above the selected region, comprising:

a narrow spectral optical radiation source for delivering radiation of a wavelength between 600 nm and 1850 nm and at a power density of between approximately 0.2 W/cm$^2$ and 5 W/cm$^2$ to the patient's skin, the wavelength and the power density both varying as a function of the depth of the selected region; and a cooling mechanism for cooling tissue above said selected region to a temperature below that of said selected region.

48. Apparatus for treating at least a selected region at depth of a patient while protecting tissue above the selected region, comprising:

a narrow spectral optical radiation source for delivering radiation of a wavelength between about 600 nm and about 1850 nm, at a power density of between approximately 0.2 W/cm$^2$ and 50 W/cm$^2$ to the patient's skin for a duration between about two seconds and two hours, the wavelength, duration and power density all varying as a function of the depth of the selected region; and a cooling mechanism for cooling tissue above said selected region to a temperature below that of said selected region.

49. The apparatus of claim 48, wherein said narrow spectral optical radiation source is a monochromatic source.

50. The apparatus of claim 48, wherein said narrow spectral optical radiation source is a laser.

51. The apparatus of claim 50, wherein said laser is a fiber laser or a diode laser.

52. The apparatus of claim 48, wherein said narrow spectral optical radiation source is an LED.

53. A method for treating subdermal fat at depth of a patient's body, comprising:

(a) selectively delivering radiation at a power density between approximately 0.2 W/cm$^2$ and 50 W/cm$^2$ to a selected region of subdermal fat of the patient's body for a duration of about two seconds to about two hours, both said power density and said duration varying with the depth of said selected region; and (b) concurrently cooling patient tissue above said selected region to a temperature below that of the selected region.

54. The method of claim 53, wherein said radiation has a wavelength selected from the group of about 925 nm, about 1206 nm, about 1730 nm and about 2300 nm.

55. A method for treating at least a selected region at depth of a patient's body while protecting tissue above the selected region, comprising:

(a) selectively delivering radiation of a wavelength between about 600 nm and about 1850 nm and at a power density between approximately 0.2 W/cm$^2$ and 5 W/cm$^2$ to the patient's body above said selected region, both said power density and wavelength varying as a function of the depth of said selected region; and (b) concurrently cooling patient tissue above said selected region to a temperature below that of the selected region.

56. A method as claimed in claim 36 wherein said selected region contains subdermal fat; and wherein said radiation at least includes at least one wavelength selectively absorbed by fat.

* * * * *